United States Patent
Ferreira et al.

(10) Patent No.: US 6,855,476 B2
(45) Date of Patent: Feb. 15, 2005

(54) PHOTOACID GENERATORS FOR USE IN PHOTORESIST COMPOSITIONS

(75) Inventors: Lawrence Ferreira, Fall River, MA (US); Andrew J. Blakeney, Seekonk, MA (US); Gregory Dominic Spaziano, Providence, RI (US); Ognian Dimov, Cranston, RI (US); J. Thomas Kocab, Wyoming, RI (US); John P. Hatfield, Hope Valley, RI (US)

(73) Assignee: Arch Specialty Chemicals, Inc., Norwalk, CT (US)

( * ) Notice: Subject to any disclaimer, the term of this patent is extended or adjusted under 35 U.S.C. 154(b) by 288 days.

(21) Appl. No.: 10/117,693

(22) Filed: Apr. 5, 2002

(65) Prior Publication Data

US 2002/0197558 A1 Dec. 26, 2002

Related U.S. Application Data

(60) Provisional application No. 60/281,652, filed on Apr. 5, 2001.

(51) Int. Cl.$^7$ .............................. G03F 7/038; G03F 7/26
(52) U.S. Cl. .................... 430/270.1; 430/325; 430/913; 430/914; 430/921; 430/922; 568/19; 568/27; 568/28
(58) Field of Search .............................. 568/19, 27, 28; 430/270.1, 325, 913, 914, 921, 922

(56) References Cited

U.S. PATENT DOCUMENTS

| | | | |
|---|---|---|---|
| 4,736,055 A | | 4/1988 | Dietliker et al. |
| 6,090,518 A | | 7/2000 | Niinomi et al. |
| 6,203,965 B1 | | 3/2001 | Cameron et al. |
| 2002/0051933 A1 | * | 5/2002 | Kodama et al. ......... 430/270.1 |
| 2002/0102491 A1 | * | 8/2002 | Kodama et al. ......... 430/270.1 |
| 2003/0113659 A1 | | 6/2003 | Hatakeyama et al. |
| 2003/0194640 A1 | * | 10/2003 | Sato ........................ 430/270.1 |

FOREIGN PATENT DOCUMENTS

| | | | | |
|---|---|---|---|---|
| DD | 295 421 A5 | | 10/1999 | |
| EP | 794457 A2 | * | 9/1997 | ........... G03F/7/004 |
| EP | 1199603 A1 | * | 4/2002 | ........... G03F/7/004 |
| JP | 2002139838 A | * | 5/2002 | ........... G03F/7/039 |

OTHER PUBLICATIONS

English language abstract of DE 295241.*
Caplus Abstract Document No. 108:5551 "A Novel Method for Carbon–Carbon Bond Formation . . . " Chen et al.
Caplus Abstract Document No. 100:102711 "Perfluroro and Polyfluorosulfonic Acids . . . " Su et al.
Caplus Abstract Document No. 101:22953 "Reaction of 2,2,3,3–Tetrafluoropropyl . . . " Li et al.
Caplus Abstract Document No. 132:194543 "Some New Reactions of Poly(Per)Fluoroalkanesulfonyl . . . " Tian et al.

* cited by examiner

*Primary Examiner*—Amanda Walke
(74) *Attorney, Agent, or Firm*—Ohlandt, Greeley, Ruggiero & Perle

(57) ABSTRACT

A photoacid compound having the following general structure:

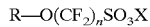

$$R-O(CF_2)_nSO_3X$$

wherein n is an integer between about 1 to 4; R is selected from the group consisting of: substituted or unsubstituted $C_1$–$C_{12}$ linear or branched alkyl or alkenyl, substituted or unsubstituted araalkyl, substituted or unsubstituted aryl, substituted or unsubstituted bicycloalkyl, substituted or unsubstituted tricycloalkyl, hydrogen, alkyl sulfonic acid, substituted or unsubstituted perfluoroalkyl, the general structure $F((CF_2)_pO)_m(CF_2)_q$— wherein p is between about 1 to 4, m is between about 0 to 3 and q is between about 1 to 4, and substituted or unsubstituted partially fluorinated alkyl, halofluoroalkyl, perfluoroalkylsulfonic, or glycidyl; and X is selected from the group consisting of: organic cations and covalently bonded organic radicals.

29 Claims, No Drawings

PHOTOACID GENERATORS FOR USE IN PHOTORESIST COMPOSITIONS

RELATED APPLICATION

This application claims priority from Provisional Application Ser. No. 60/281,652, filed on Apr. 5, 2001.

FIELD OF THE INVENTION

This invention relates to new photoacid generator compounds ("PAGs") and photoresist compositions that comprise such compounds. Specifically, the invention relates to novel classes of photoacid generators that produce a fluorinated alkyl sulfonic acid having a short perfluoroalkyl chain attached to an ether linkage. This ether linkage connects the fluorinated alkyl portion of the molecule with a variety of other substituents.

BACKGROUND TO THE INVENTION

Photoresists are light sensitive compositions that produce chemical changes in the compositions after exposure to light. These changes allow chemical differentiation between exposed and unexposed areas using a developer, typically an aqueous alkali solution. When a mask having a pattern of transmissive and reflective areas is used, this chemical differentiation produced relief images. The produced images allow transfer of the image into underlying substrates for electronic device manufacture or to other materials in a printing process.

In recent years, advanced resists comprise a photosensitive acid generator (PAG), a polymer matrix, and sometimes additives. Acid sensitive groups that inhibit dissolution of the polymer in developer are present on the additive or on the polymer. Upon exposure, the acid generated from the PAG catalyzes the removal of the acid sensitive group that is inhibiting dissolution in the developer. One acid proton will catalyze reaction at many different sites, so the technique is called "chemical amplification". Photoresists of these type can be found, e.g. in U.S. Pat. No. 6,120,977, U.S. Pat. No. 6,136,504, U.S. Pat. No. 6,013,416, U.S. Pat. No. 5,985,522, U.S. Pat. No. 5,693,453, and U.S. Pat. No. 4,491,628.

Various classes of PAGs have been utilized in acid catalyzed photopolymer systems. Particularly favored are those that produce a sulfonic acid. Numerous types of PAGs have been demonstrated to produce sulfonic acids upon irradiation. Examples of some of the classes are shown below. Particularly favored are those PAGs of the formulae:

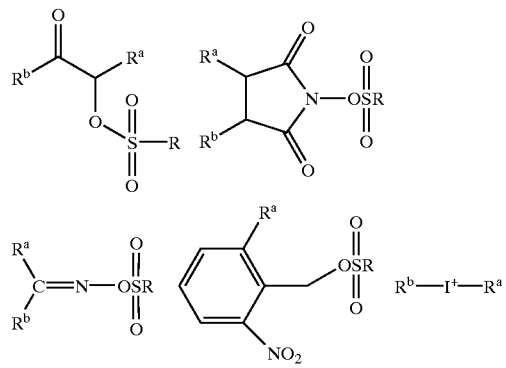

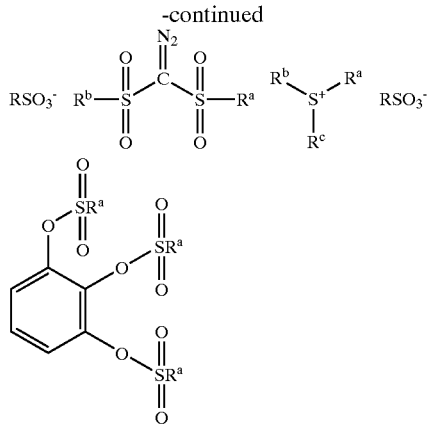

where R is a perfluoroalkyl because of the strong acidity of the perfluoroalkyl sulfonic acids and other factors. Particularly preferred is perluorooctanesulfonic acid because of the low diffusion length. However, recently, the EPA has raised concerns regarding health and environmental impact of some long chain perfluorinated sulfonic acid salts (viz., perfluorooctanesulfonate). Shorter perfluoroalkyl chains sulfonic acids do not address the combination of health and performance concerns. As the perfluoroalkyl chain becomes shorter it is believed to increase the diffusion length. Triflic acid ($R=CF_3$) has been shown to be volatile under some processing conditions, which can give poor results. In addition, the long-term viability and availability of other, shorter chain perfluorinated sulfonic acid salts is also in question due to the environmental and health issues. It is desirable to have sulfonic acids which have comparable acidity (i.e., pKa) and diffusion lengths to the larger perfluorinated sulfonic acids but without a heavily fluorinated alkyl chain directly attached to the sulfonic acid moiety.

SUMMARY OF THE INVENTION

A photoacid compound having the following general structure:

$$R\text{—}O(CF_2)_n SO_3 X$$

wherein n is an integer between about 1 to 4; R is selected from the group consisting of: substituted or unsubstituted $C_1$–$C_{12}$ linear or branched alkyl or alkenyl, substituted or unsubstituted araalkyl, substituted or unsubstituted aryl, substituted or unsubstituted bicycloalkyl, substituted or unsubstituted tricycloalkyl, hydrogen, alkyl sulfonic acid, substituted or unsubstituted perfluoroalkyl, the general structure $F((CF_2)_p O)_m (CF_2)_q$— wherein p is between about 1 to 4, m is between about 0 to 3 and q is between about 1 to 4, and substituted or unsubstituted partially fluorinated alkyl, halofluoroalkyl, perfluoroalkylsulfonic, or glycidyl; and X is selected from the group consisting of: organic cations and covalently bonded organic radicals.

A photoresist composition comprising: (a) a polymer; and (b) a photoacid compound having the following general structure:

$$R\text{—}O(CF_2)_n SO_3 X$$

wherein n is an integer between about 1 to 4; R is selected from the group consisting of: substituted or unsubstituted $C_1$–$C_{12}$ linear or branched alkyl or alkenyl, substituted or unsubstituted araalkyl, substituted or unsubstituted aryl, substituted or unsubstituted bicycloalkyl, substituted or unsubstituted tricycloalkyl, hydrogen, alkyl sulfonic acid, substituted or unsubstituted perfluoroalkyl, the general structure $F((CF_2)_pO)_m(CF_2)_q$— wherein p is between about 1 to 4, m is between about 0 to 3 and q is between about 1 to 4, and substituted or unsubstituted partially fluorinated alkyl, halofluoroalkyl, perfluoroalkylsulfonic, or glycidyl; and X is selected from the group consisting of: organic cations and covalently bonded organic radicals. Optionally, the photoresist composition may also include at least one additive selected from the group consisting of: surfactants, bases, dyes, plasticizers, and dissolution inhibitors.

A method for fabricating an integrated circuit which comprises: depositing a photoresist composition on a substrate, wherein the photoresist composition comprises: (a) a polymer; and (b) a photoacid compound having the following general structure:

wherein n is an integer between about 1 to 4; R is selected from the group consisting of: substituted or unsubstituted $C_1-C_{12}$ linear or branched alkyl or alkenyl, substituted or unsubstituted araalkyl, substituted or unsubstituted aryl, substituted or unsubstituted bicycloalkyl, substituted or unsubstituted tricycloalkyl, hydrogen, alkyl sulfonic acid, substituted or unsubstituted perfluoroalkyl, the general structure $F((CF_2)_pO)_m(CF_2)_q$— wherein p is between about 1 to 4, m is between about 0 to 3 and q is between about 1 to 4, and substituted or unsubstituted partially fluorinated alkyl, halofluoroalkyl, perfluoroalkylsulfonic, or glycidyl; and X is selected from the group consisting of: organic cations and covalently bonded organic radicals; and irradiating the photoresist composition, thereby generating a fluorinated alkyl sulfonic acid with a short perfluoroalkyl chain attached to an ester linkage.

DETAILED DESCRIPTION OF THE PREFERRED EMBODIMENT

The present invention relates to novel classes of photoacid generators that produce a fluorinated alkyl sulfonic acid with a short perfluoroalkyl chain attached to an ether linkage after irradiation and resists comprising them. Photoacid generators of this type have been found useful in chemically amplified resist systems. Resists containing these novel PAGs have been shown to have superior resolution, depth of focus, and more vertical profiles.

The fluorinated alkyl sulfonic acid with a short perfluoroalkyl chain attached to an ether linkage produced from the PAGs in this invention can be described by the following generic structure:

R can be substituted or unsubstituted $C_1-C_{12}$ linear or branched alkyl or alkenyl, substituted or unsubstituted araalkyl, substituted or unsubstituted aryl, substituted or unsubstituted bicycloalkyl, substituted or unsubstituted tricycloalkyl, hydrogen, lkyl sulfonic acid, substituted or unsubstituted perfluoroalkyl, the general structure $F((CF_2)_pO)_m(CF_2)_q$— wherein p is between about 1 to 4, m is between bout 0 to 3 and q is between about 1 to 41, substituted or unsubstituted partially fluorinated alkyl, halofluoroalkyl, perfluoroalkylsulfonic, or glycidyl.

Examples of suitable sulfonic acids (or salts of the acids) include but are not limited to:
1,1,2,2-tetrafluoro-2-(trifluoromethoxy)-ethanesulfonic acid;
1,1,2,2-tetrafluoro-2-(1,1,2,2-tetrafluoro-2-iodoethoxy)-ethanesulfonic acid;
(8-chloro-1,1,2,2,3,3,4,4,5,5,6,6,7,7,8,8-hexadecafluorooctyl)oxy]difluoromethanesulfonic acid;
1,1,2,2,3,3-hexafluoro-3-[(trifluoroethenyl)oxy]-1-propanesulfonic acid anion;
1,1,2,2-tetrafluoro-2-[(heptadecafluorooctyl)oxy]-ethanesulfonic acid;
2,2'-[(difluoromethylene)bis(oxy)]bis[1,1,2,2-tetrafluoro-ethanesulfonic acid;
2-[(1,1,2,2,3,3,4,4,5,5,6,6-dodecafluoro-6-sulfinohexyl)oxy]-1,1,2,2-tetrafluoroethanesulfonic acid;
2-(4-ethenylphenoxy)-1,1,2,2-tetrafluoroethanesulfonic acid;
1,1,2,2-tetrafluoro-2-(1,1,2,2,3,4,4,4-octafluoro-3-ethanesulfonic acid;
ethanesulfonic acid, 1,1,2,2-tetrafluoro-2-[1,2,2-trifluoro-1-methyl-2-[1,2,2-trifluoro-1-methyl-2-(pentafluoroethoxy)ethoxy]ethoxy]-ethanesulfonic acid;
1,1,2,3,3,4,4,5,5,6,6,7,7,8,8,9,9,10,10-nonadecafluoro-10-(1,1,2,2-tetrafluoro-2-sulfoethoxy)-1-decanesulfonic acid;
4-(4-chloro-1,1,2,2,3,3,4,4-octafluorobutoxy)-1,1,2,2,3,3,4,4-octafluoro-1-butanesulfonic acid;
3-[1-[difluoro[(trifluoroethenyl)oxy]methyl]-1,2,2,2-tetrafluoroethoxy]-1,1,2,2,3,3-hexafluoro-1-propanesulfonic acid;
1,1,2,2,3,3-hexafluoro-3-[1,1,2,2,3,3-hexafluoro-3-[1,1,2,2,3,3-hexafluoro-3-[trifluoroethenyl)oxy]propoxy]propoxy]-1-propanesulfonic acid;
1,1,2,2-tetrafluoro-2-[1,2,2,2-tetrafluoro-1-(trifluoromethyl)ethoxy]-ethanesulfonic acid;
1,1,2,2-tetrafluoro-2-(nonafluorobutoxy)-ethanesulfonic acid;
5-(1,1,2,2-tetrafluoro-2-sulfoethoxy)-1,3-benzenedicarboxylic acid-1,3-dimethyl ester;
2-[1-[difluoro[1,2,2,3,3-pentafluoro-1-(1,1,2,2-tetrafluoropropyl)butoxy]methyl]-1,2,2,2-tetrafluoroethoxy]-1,1,2,2,-tetrafluoro-ethanesulfonic acid;
1,1,2,2-tetrafluoro-2-[1,1,2,2,3,3-hexafluoro-3-[(trifluoroethenyl)oxy]propoxy]-ethanesulfonic acid;
2,2'-[(1,1,2,2,3,3,4,4-octafluoro-1,4-butanediyl)bis(oxy)]bis[1,1,2,2-tetrafluoro-ethanesulfonic acid;
2-(2,2-dichloro-1,1,2-trifluoroethoxy)-1,1,2,2-tetrafluoro-ethanesulfonic acid;
2-fluoro-(1,1,2,2-tetrafluoro-2-2-sulfoethoxy)-propanedioic acid;
1,1,2,2-tetrafluoro-2-[(1,1,2,2,3,3,4,4,5,5,6,6,7,7,8,8-hexadecafluoro-8-iodooctyl)oxy]-ethanesulfonic acid;
2-[1-[(1,2-dichloro-1,2,2-trifluoroethoxy)difluoromethyl]-1,2,2,2-tetrafluoroethoxy]-1,1,2,2,-tetrafluoro-ethanesulfonic acid;
2,2'-oxybis 1,1,2,2-tetrafluoro-ethanesulfonic acid;
2-(chlorodifluoromethoxy)-1,1,2,2-tetrafluoro-ethanesulfonic acid;
2,2'-[(1,1,2,2,3,3,4,4,5,5,6,6,7,7,8,8,19,19,20,20,21,21,22,22,23,23,24,24,25,25,26,26-dotriacontafluoro-1,26-hexacosanediyl)bis(oxy)]bis[1,1,2,2-tetrafluoro-ethanesulfonic acid];
1,1,2,2-tetrafluoro-2-(2-propenyloxy)ethanesulfonate;
2-[1-[difluoro(1,2,2,2-tetrafluoroethoxy)methyl]-1,2,2,2-tetrafluoroethoxy]-1,1,2,2-tetrafluoro-ethanesulfonic acid;
1,1,2,2,3,3,-hexafluoro-3-[1,2,2-trifluoro-2-[(triflorethenyl)oxy]ethoxy]-1-propanesulfonic acid;
1,1,2,2-tetrafluoro-2-[1,1,2,2-tetrafluoro-2-[1,1,2,2-tetrafluoro-2-(pentafluoroethoxy)ethoxy]ethoxy]-ethanesulfonic acid;

1,1,2,2-tetrafluoro-2-[1,1,2,2-tetrafluoro-2-[1,1,2,2-tetrafluoro-2-[(trifluoroethenyl)oxy]ethoxy'ethoxy]-ethanesulfonic acid;

1,1,2,2-tetrafluoro-2-[1,1,2,2-tetrafluoro-2-[1,1,2,2-tetrafluoro-2-(pentafluoroethoxy)ethoxy]ethoxy] ethanesulfonic acid;

1,1,2,2-tetrafluoro-2-[1,1,2,2-tetrafluoro-2-[1,1,2,2-tetrafluoro-2-[(trifluoroethenyl)oxy]ethoxy]ethoxy]-ethanesulfonic acid;

1,1,2,2-tetrafluoro-2-(2,2,3,3,3-pentafluoropropoxy)-ethanesulfonic acid;

2-[1-[[2-(4-cyanophenoxy)-1,2,2-trifluoroethoxy]difluoromethyl]-1,2,2,2-tetrafluoroethoxy]-1,1,2,2-tetrafluoro-ethanesulfonic acid;

2-[1-[difluoro(trifluoromethoxy)methyl]-1,2,2,2-tetrafluoroethoxy]-1,1,2,2-tetrafluoro-ethanesulfonic acid;

2-(1,2-dichloro-1,2,2-trifluoroethoxy)-1,1,2,2-tetrafluoro-ethanesulfonic acid;

1,1,2,2-tetrafluoro-2-(oxiranylmethoxy)-ethanesulfonic acid, lithium salt;

2-[1-[difluoro[1,2,3,3,3-pentafluoro-1-propenyl)oxy]methyl]-1,2,2,2-tetrafluoroethoxy]-1,1,2,2-tetrafluoro-ethanesulfonate;

1,1,2,2-tetrafluoro-2-(trichloromethoxy)-ethanesulfonic acid;

1,1,2,2-tetrafluoro-2-[(1,1,2,2,3,3,4,4,5,5,6,6,7,7,8,8-hexadecafluoro-19-hydroxynonadecyl)oxy]-ethanesulfonic acid;

2-(2-bromo-1,1,2,2-tetrafluoroethoxy)-1,1,2,2-tetrafluoro-ethanesulfonic acid;

1,1,2,2-tetrafluoro-2-(1,1,2,2,3,4,4,4-octafluorobutoxy)-ethanesulfonic acid;

2-[2-(1-bromo-1,2,2,2-tetrafluoroethoxy)-1,2,2-trifluoro-1-(trifluoromethyl)ethoxy]-1,1,2,2-tetrafluoro-ethanesulfonic acid;

1,1,2,2-tetrafluoro-2-[(1,1,2,2-tetrafluoro-3-butenyl)oxy]-ethanesulfonic acid;

[1-[difluoro[(trifluoroethenyl)oxy]methyl]-1,2,2,2-tetrafluoroethoxy]difluoro-methanesulfonic acid;

1,1,2,2-tetrafluoro-2-(pentafluoroethoxy)-ethanesulfonic acid;

2,2'-[methylene(oxy)]bis[1,1,2,2-tetrafluoro-ethanesulfonic acid;

1,1,2,2-tetrafluoro-2-(1,1,2,2,3,3,4,4-octafluoro-4-iodobutoxy)-ethanesulfonic acid;

12,12,13,13,14,14,15,15,16,16,17,17,18,18,19,19-hexadecafluoro-19-(1,1,2,2-tetrafluoro-2-sulfoethoxy)-nonadecanoic acid;

1,1,2,2-tetrafluoro-2-[(1,1,2,2-tetrafluoro-4-iodooctyl)oxy]-ethanesulfonic acid;

1,1,2,2-tetrafluoro-2-2[1,1,2,2-tetrafluoro-2-[(trifluoroethenyl)oxy]ethoxy]-ethanesulfonic acid;

2-[1-[[1-[[2,2,3,3,3-pentafluoro-1-(pentafluoroethyl)-1-(trifluoromethyl)propyl]methyl]-1,2,2,2-tetrafluoroethoxy]difluoromethyl]-1,1,2,2-tetrafluoroehtoxy]-1,1,2,2-tetrafluoro-ethanesulfonic acid;

1,1,2,2-tetrafluoro-2-[1,1,2,3,3,3-hexafluoro-2-[(trifluoroethenyl)oxy]propoxy]-ethanesulfonic acid;

2-[(8-chloro-1,1,2,2,3,3,4,4,5,5,6,6,7,7,8,8-hexadecafluorooctyll)oxy]-1,1,2,2-tetrafluoro-ethanesulfonic acid;

1,1,2,2,3,3-hexafluoro-3-pentafluoroethoxy)-1-propanesulfonic acid;

1,1,2,2-tetrafluoro-2-(1,1,2,2-tetrafluoroethoxy)-ethanesulfonic acid;

2-(4-bromophenoxy)-1,1,2,2-tetrafluoro-ethanesulfonic acid;

1,1,2,2-tetrafluoro-2-[(tridecafluorohexyl)oxy]-ethanesulfonic acid;

1,1,2,2-tetrafluoro-2-(1,1,2,2,3,3,4,4-octafluoro-4-sulfinobutoxy)-ethanesulfonic acid;

12,12,13,13,14,14,15,15,16,16,17,17,18,18,19,19-hexadecafluoro-10-iodo-19-(1,1,2,2-tetrafluoro-2-sulfoethoxy)-nonadecanoic acid;

1,1,2,2-tetrafluoro-2-[1,1,2,2,3,3,3-hexafluoro-2-(pentafluoroethoxy)propxy]-ethanesulfonic acid;

2-[1-[[1-[difluoro[(trifluoroethenyl)oxy]methyl]-1,1,2,2-tetrafluoroethoxy]difluoromethyl]-1,1,2,2-tetrafluoroethoxy]-1,1,2,2-tetrafluoro-ethanesulfonic acid;

1,1,2,2-tetrafluoro-2-[2-(2-propenyloxy)ethoxy] ethanesulfonic acid;

1,1,2,2,3,3-hexafluoro-3-[(trifluoroethenyl)oxy]-1-propanesulfonic acid;

1,1,2,2-tetrafluoro-2-(1,1,2,2-tetrafluoroethoxy)-ethanesulfonic acid;

2-[1-[difluoro[1,2,2,3,3,3-hexafluoro-1-(pentafluoroethyl) propoxy]methyl]-1,1,2,2-tetrafluoroethoxy]-1,1,2,2-tetrafluoro-ethanesulfonic acid;

difluoro(1,1,2,2-tetrafluoro-2-sulfoethoxy)-acetic acid;

5-[1,1,2,2-tetrafluoro-2-[1,1,2,3,3,3-hexafluoro-2-(1,1,2,2-tetrafluoro-2-sulfoethoxy)propoxy]ethoxy]-1,3-benzenedicarboxylic acid)1,3-dimethyl ester;

difluoro(pentafluoroethoxy)-methanesulfonic acid;

2-[(6-chloro-1,1,2,2,3,3,4,4,5,5,6,6-dodecafluorohexyl)oxy]-1,1,2,2-tetrafluoro-ethanesulfonic acid;

12,12,13,13,14,14,15,15,16,16,17,17,18,18,19,19-hexadecafluoro-19-(1,1,2,2-tetrafluoro-2-sulfoethoxy) nonadecyl bromoacetate;

2-[1-[difluoro(pentafluoroethoxy)methyl]-1,1,2,2-tetrafluoroethoxy]-1,1,2,2-tetrafluoro-ethanesulfonic acid;

2,3,3,3-tetrafluoro-2-[1,1,2,3,3,3-hexafluoro-2-[1,1,2,3,3,3-hexafluoro-2-(1,1,2,2-tetrafluoro-2-sulfoethoxy) propoxy]propoxy]-propionic acid;

1,1,2,2-tetrafluoro-2-[(1,1,2,2,3,3,4,4,5,5,6,6,7,78,8-hexadecafluorotetradecyl)oxy]-ethanesulfonic acid;

2-(2-chloro-1,1,2,2-tetrafluoroethoxy)-1,1,2,2-tetrafluoro-ethanesulfonic acid;

2-[1-[[1-[difluoro(pentafluoroethoxy)methyl]-1,1,2,2-tetrafluoro-ethoxy]difluoromethyl]-1,1,2,2-tetrafluoroethoxy]-1,1,2,2-tetrafluoro-ethanesulfonic acid;

1,1,2,2-tetrafluoro-2-[1,1,2,3,3,3-hexafluoro-2-[1,1,2,3,3,3-hexafluoro-2-(pentafluoroethoxy)propoxy]propoxy]-ethanesulfonic acid;

1,1,2,2-tetrafluoro-2-(1,1,2,2-tetrafluoro-2-sulfinoethoxy)-ethanesulfonic acid;

2-[(1,1,2,2,3,3,4,4,5,5,6,6-dodecafluoro-6-iodohexyl)oxy]-1,1,2,2-tetrafluoro-ethanesulfonic acid;

1,1,2,2,3,3,4,4-octafluoro-4-(1,1,2,2-tetrafluoro-2-sulfoethoxy)-1-butanesulfonic acid;

2-[(6-brom-1,1,2,2,3,3,4,4,5,5,6,6-dodecafluorohexyl)oxy]-1,1,2,2-tetrafluoro-ethanesulfonic acid;

1,1,2,2-tetrafluoro-2-[(1,1,2,2-tetrafluoro-4-iodononyl)oxy]-ethanesulfonic acid;

1,1,2,2-tetrafluoro-2-[1,1,2,2-tetrafluoro-2-(pentafluoroethoxy)ethoxy]-ethanesulfonic acid;

1,1,2,2-tetrafluoro-2-(2,2,2-trifluoroethoxy)ethanesulfonic acid; and

2-[1-[difluoro((trifluoroethenyl)oxy]methyl]-1,1,2,2-tetrafluoroethoxy]-1,1,2,2-tetrafluoro-ethanesulfonic acid.

Examples of PAGs of this invention made from the fluorinated alkyl sulfonic acids with a short perfluoroalkyl chain attached to an ether linkage may be either A or B below.

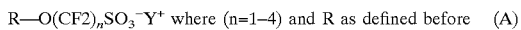

R—O(CF2)$_n$SO$_3^-$Y$^+$ where (n=1–4) and R as defined before  (A)

where Y is any organic cation, which upon exposure of the salt to radiation, especially radiation of about 248 nm or 193 nm, generates a free fluoro-substituted sulfonic acid; or

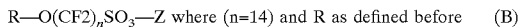

R—O(CF2)$_n$SO$_3$—Z where (n=14) and R as defined before  (B)

where Z is any covalently bonded organic radical, which upon exposure to radiation, especially radiation of about 193 nm or 248 nm, generates a free fluoro-substituted sulfonic acid.

Y is preferably an onium cation, especially a sulfonium or iodonium cation. Z is preferably an organic group selected from a substituted or unsubstituted nitrobenzyl, phenolic, alpha-acyl ketone, alkyl, cycloalkyl, aralkyl oxime, substituted sulfonyldiazomethyl or imide radical.

Some examples include, but are not limited to the following:

Onium Salts

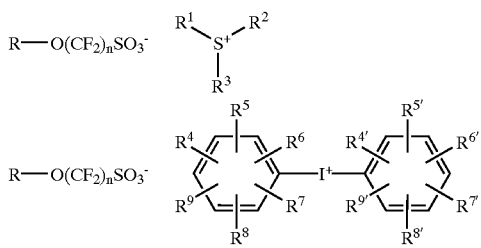

where R$^1$–R$^3$ can be individually selected from substituted or unsubstituted aryl or alkyl, R$^4$, R$^5$, R$^6$, R$^7$, R$^8$, R$^{4'}$, R$^{5'}$, R$^{6'}$, R$^{7'}$ and R$^{8'}$ can be individually selected from branched, linear, or cyclic alkyl, branched, linear, or cyclic alkoxy, halogen, hydrogen, OCO$_2$G, OCH$_2$CO$_2$G, or OG where G=an acid sensitive group such as t-butyl and R and n are defined as before. Other suitable sulfonium cations include:

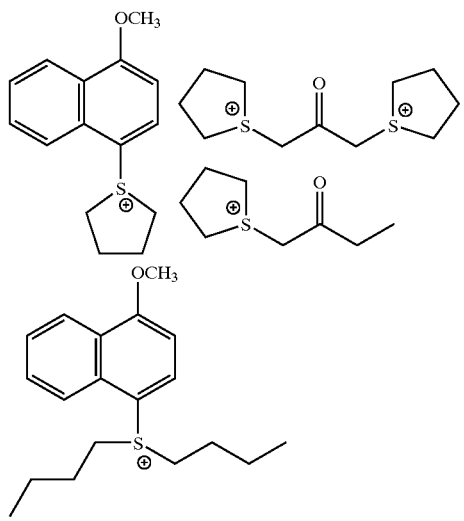

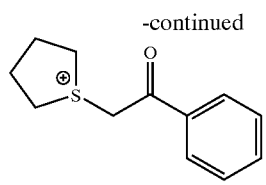

Methods for synthesis of onium salts can be found in Proc. SPIE, 3333, pp. 735–746 (1998), the Journal of Organic Chemistry, 55, 4222 (1990) and references therein which are incorporated herein by reference.

Diaryliodonium salts are prepared by reaction at −5 to 5° C. of an appropriately substituted aryl compound with potassium iodate in a mixture of 63% acetic anhydride in concentrated sulfuric acid, thereby producing diaryliodonium bisulfate. Diaryliodonium chloride is produced by reaction of a diaryliodonium bisulfate with ammonium chloride. Anion exchange of the diaryliodonium chloride with a salt of a fluorinated alkyl sulfonic acid having a short perfluoroalkyl chain attached to an ether linkage yields the desired PAG.

Triarylsulfonium salts are prepared by reaction at −5 to 5° C. of an appropriately substituted aryl sulfoxide with an aromatic compound at 50–60° C. in Eaton's Reagent (7.7% phosphorous pentoxide in methanesulfonic acid). The reaction mixture is added to distilled water and the pH of the aqueous solution is adjusted to a pH of 8 by addition of tetramethylammonium hydroxide. The aqueous solution contains the desired triarylsulfonium mesylate. Anion exchange of the aqueous solution containing the triarylsulfonium mesylate with a salt of a fluorinated alkyl sulfonic acid having a short perfluoroalkyl chain attached to an ether linkage yields the desired PAG.

Alternatively, triarylsulfonium salts can also be prepared by the copper-catalyzed condensation of diaryliodonium salts with diaryl sulfides and aryls thiols as described in the literature (J. Org. Chem., 43, 3055 (1978), Synth. Commun., 9(3), 151 (1979)), which is incorporated herein by reference.

Oxime Sulfonates

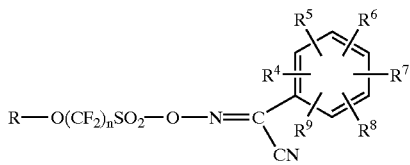

where R, n, and R$^4$–to R$^8$ are as defined before.

Methods for synthesis of oxime sulfonates can be found in U.S. Pat. No. 5,800,964 and references therein, which are incorporated herein by reference. The reaction of a cyano-substituted, N-hydroxy oxime with a fluorinated alkyl sulfonyl halide having a short perfluoroalkyl chain attached to an ether linkage is carried out in the presence of an organic amine or other suitable base in an organic solvent such as tetrahydrofuran, N,N-dimethyl formamide, N,N-dimethyl acetamide, N-methyl pyrrolidone at about 40° C. The reaction solution is stirred for 20 hours at room temperature. The resultant oxime sulfonate is isolated by adding the reaction mixture into water adjusting the pH of the solution to 14 by addition of sodium hydroxide. The organic layer is separated and discarded. The aqueous layer is acidified with hydrochloric acid followed by extraction with diethyl ether. The ether is removed by evaporation and the resulting solid purified by recrystallization from toluene.

N-hydroxyimide Sulfonates

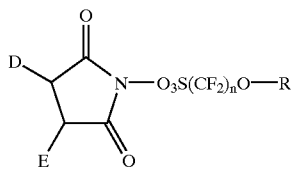

where D and E are independently H, substituted or unsubstituted aryl or together compose a substituted or unsubstituted bicyclic, or tricyclic alicyclic ring system (e.g. cyclohexene, or norbornyl) and R and n are defined as before.

Methods for synthesis of N-hydroxyimidesulfonates can be found in U.S. Pat. No. 5,965,748 and references therein, which are incorporated herein by reference. The reaction of an N-hydroxyimide with a fluorinated alkyl sulfonyl halide having a short perfluoroalkyl chain attached to an ether linkage is carried out in a polar solvent in the presence of a basic catalyst. Examples of the polar solvent include one or more of hydrophilic solvents such as acetone, tetrahydrofuran, 1,4-dioxane, 1,3-dioxolane, dimethylformamide, acetonitrile, γ-butyrolactone and dimethylsulfoxide, one or more of hydrophobic solvents such as dichloromethane and chloroform, and water including deionized water and distilled water. Examples of a basic catalyst used in this reaction included aliphatic amines such as triethylamine, cyclic amines such as pyridine, and inorganic bases such as sodium hydrogen carbonate, sodium carbonate or potassium carbonate. The reaction can usually be carried out at a temperature within a range of 20–50° C.

Nitrobenzyl Esters

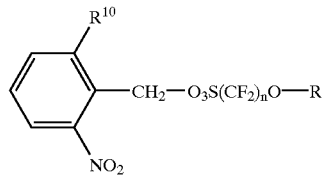

where $R^{10}$ is an electron withdrawing substituent such as halogen, $CF_3$, or nitro and R and n are defined as before.

Methods for synthesis of nitrobenzyl esters can be found in U.S. Pat. No. 5,344,742 and references therein, which are incorporated herein by reference. The reaction of a benzyl alcohol with a fluorinated alkyl sulfonyl halide having a short perfluoroalkyl chain attached to an ether linkage is carried out in the presence of an organic amine or other suitable base in an organic solvent such as acetone or dimethylformamide at about 0° C. in an inert atmosphere such as nitrogen or argon. The base is added dropwise. After the base addition is complete, the reaction solution is stirred from 0° C. to room temperature until reaction completion. The resultant nitrobenzyl ester is isolated by and purified by known techniques such as filtration followed by recrystallization.

Sulfonic Acid Esters of Phenols

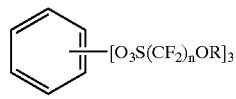

where R and n are defined as before.

Methods for synthesis of sulfonic acid esters of phenols can be found in Journal of Radiation Curing pp 2–5 (1980) and references therein, which are incorporated herein by reference. The reaction of a polyhydroxyaromatic compound and a fluorinated alkyl sulfonyl halide having a short perfluoroalkyl chain attached to an ether linkage is carried out at about 0° C. in the presence of an organic amine, typically pyridine, which also functions as the solvent for the reaction as well. The polyhydroxyaromatic compound is dissolved in pyridine. The solution is cooled and then the sulfonyl halide is added. The reaction mixture is kept at 0° C. for 24 hours. The resulting pyridinium hydrochloride salt is removed by filtration and distilled water is added to the filtrate. This mixture is kept at 0° C. overnight. The resulting solid is collected by filtration, washed with water and dried. The product can be further purified by recrystallization from a suitable organic solvent.

Alpha Sulfonyloxyketones

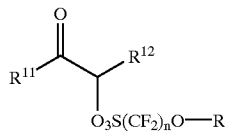

where R and n are as defined before, and $R^{11}$ or $R^{12}$ are substituted or unsubstituted alkyl or aryl.

Methods for synthesis of alpha sulfonyloxyketones can be found in EP 1041442 and references therein, which are incorporated herein by reference.

The reaction of a thioketone and a suitable alkyl halide is carried out in nitromethane at about 15° C. for 2 hours. A solution of nitromethane and the silver salt of a fluorinated alkyl sulfonic acid having a short perfluoroalkyl chain attached to an ether linkage is added dropwise, followed by stirring the mixture for 18 hours at the same temperature. Then, silver halide precipitate is filtered off and the filtrate concentrated to approximately 2% of its original volume. The concentrated solution is added into diethyl ether. The resulting precipitate is filtered off, washed with diethyl ether and dried.

Bis Sulfonyl Diazomethanes

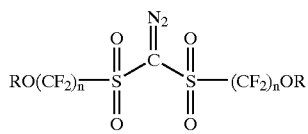

where R and n are as defined previously. Each R may be the same or different.

Methods of synthesis for bissulfonyl diazomethanes can be found in U.S. Pat. No. 5,350,660 and references therein, which are incorporated herein by reference.

A fluorinated alkyl mercaptan having a short perfluoroalkyl chain attached to an ether linkage is added to an ethanolic solution of potassium hydroxide. Then methylene chloride is added to this mixture and reacted with stirring at 45–55° C. for 6 hours. The reaction mixture is diluted with ethanol. Sodium tungstate is then added to the reaction mixture. 30% hydrogen peroxide is added dropwise to this solution at 45–50° C. The mixture is reacted with stirring for 4 hours. The mixture is diluted with water. The precipitate is filtered and recrystallized from ethanol to yield the desired bis sulfonylmethane.

The bis sulfonylmethane is dissolved in a 60% aqueous ethanol solution containing sodium hydroxide. An ethanolic solution of p-toluenesulfonyl azide is then added dropwise at 5–10° C., the reaction is stirred at room temperature for 7 hours. The resulting precipitate is filtered and recrystallized from acetonitrile to give the desired bis sulfonyldiazomethane.

Specific examples of the PAGs of this invention include but are not limited to those shown below.

PAG 1

PAG 2

PAG 3

PAG 4

PAG 5

PAG 6

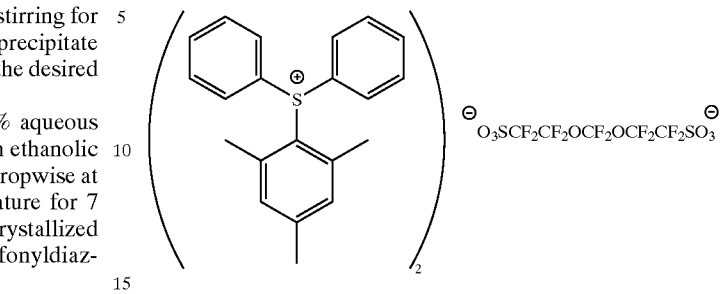

PAG 7

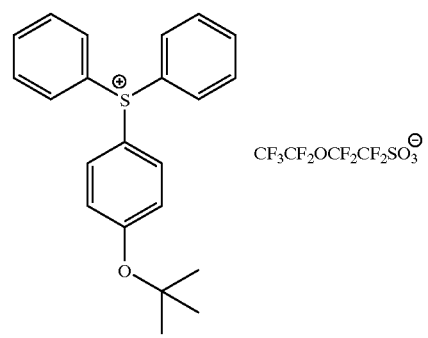

PAG 8

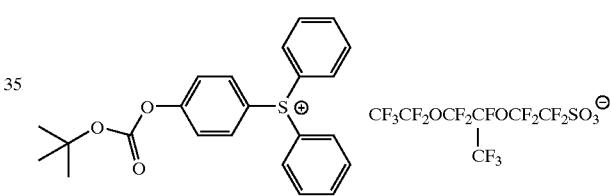

PAG 9

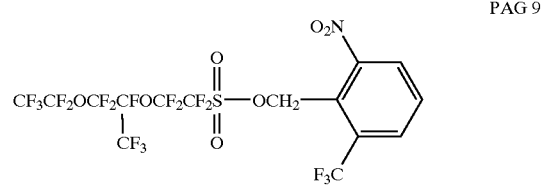

PAG 10

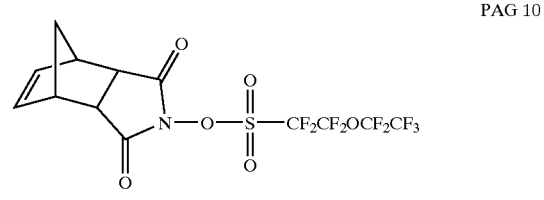

PAG 11

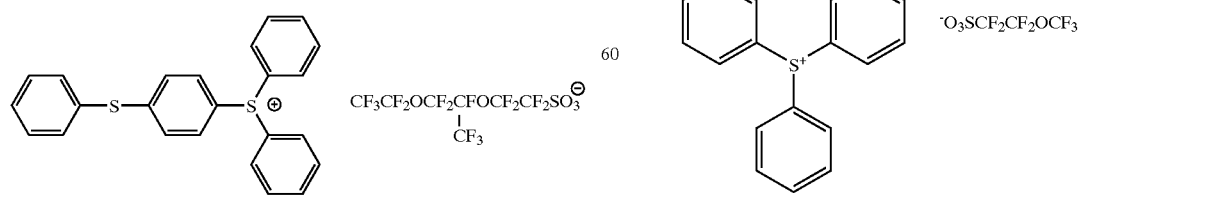

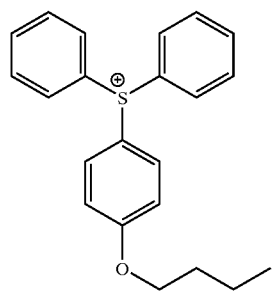
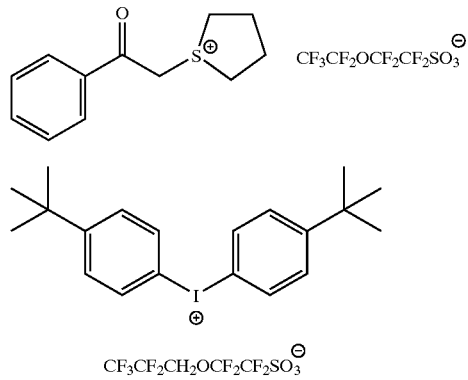
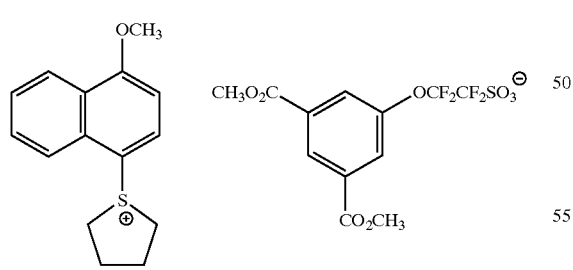
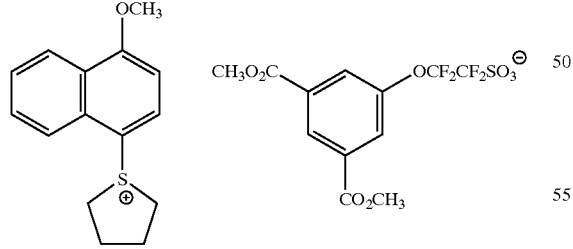

PAG 12
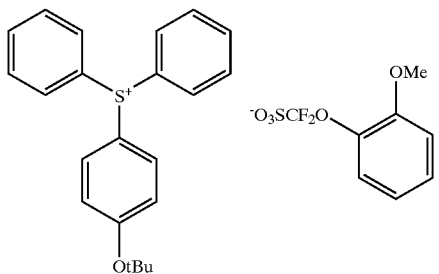

PAG 13
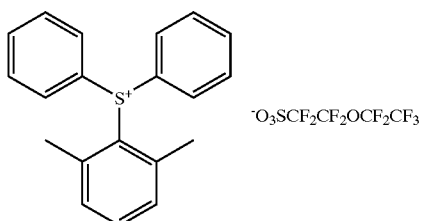

PAG 14
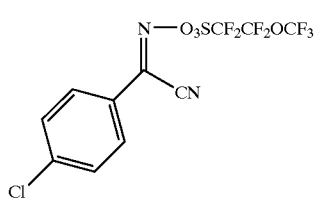

PAG 15
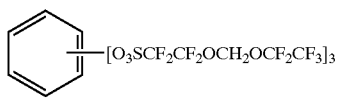

PAG 16
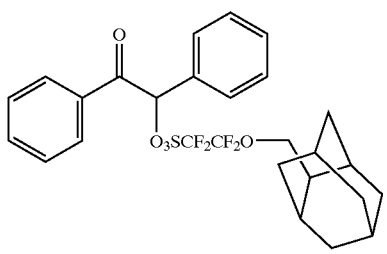

PAG 17
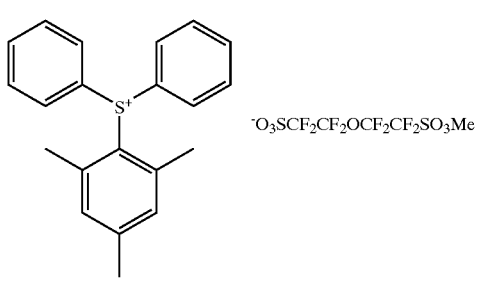

PAG 18
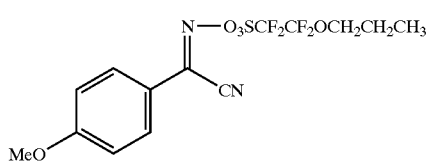

PAG 19
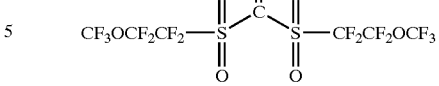

PAG 20
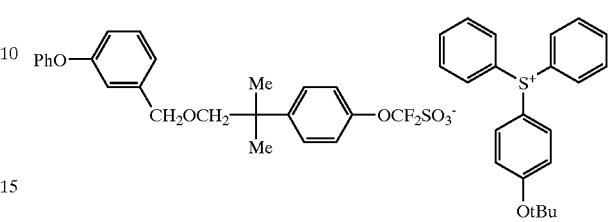

Another aspect of this invention is the use of these PAGs in photosensitive compositions. Typically these compositions would comprise a PAG of the invention and a polymer, and an optional additive with at least one of the components containing alkali solubilizing groups protected by an acid sensitive group. These photosensitive compositions may contain other additives such as bases, dyes, surfactants, and the like.

The photoacid generator may be used alone or in combination with one or more additional photoacid generators. The percentage of each photoacid generator in photoacid generator mixtures is between about 10% to about 90% of the total photoacid generator mixture. Preferred photoacid generator blends contain about 2 or 3 different photoacid generators. Such blends may be of the same class or different classes. Examples of preferred class blends include PAGs according to the present invention with additional PAGs of the present invention, with sulfonium salts, bissulfonyldiazomethane compounds, imidosulfonates, or iodonium salts.

Specific examples of other photoacid generators which may be blended with the PAGs of the present invention include, but are not limited to: triphenylsulfonium perfluorooctanesulfonate, triphenylsulfonium perfluorobutane-phenyldiphenysulfonium perfluorooctanesulfonate, 4-n-butoxyphenyldiphenylsulfonium perfluorobutanesulfonate, 2,4,6-trimethylphenyldiphenylsulfonium perfluorobutanesulfonate, 2,4,6-trimethylphenyldiphenylsulfonium benzene-sulfonate, 2,4,6-trimethylphenyldiphenylsulfonium 2,4,6-triisopropylbenzene-sulfonate, phenylthiophenyldiphenylsulfonium 4-dodecylbenzensulfonic acid, tris(-t-butylphenyl)sulfonium perfluorooctanesulfonate, tris(-t-butylphenyl)-sulfonium perfluorobutanesulfonate, tris(-t-butylphenyl)sulfonium 2,4,6-triisopropylbenzenesulfonate, tris(-t-butylphenyl)sulfoniumn benzenesulfonate, and phenylthiophenyldiphenylsulfonium perfluorooctane-sulfonate.

Examples of suitable iodonium salts for use as co-PAGs in the present invention include, but are not limited to, diphenyl iodonium perfluorobutanesulfonate, bis-(t-butylphenyl)iodonium perfluorobutanesulfonate, bis-(t-butylphenyl)iodonium perfluorooctanesulfonate, diphenyl iodonium perfluorooctanesulfonate, bis-(t-butylphenyl) iodonium benzenesulfonate, bis-(t-butylphenyl)iodonium 2,4,6-triisopropylbenzenesulfonate, and diphenyliodonium 4-methoxybenzensulfonate.

Further examples of suitable photoacid generators for use as co-PAGs in accordance with the present invention are bis(p-toluenesulfonyl)diazomethane, methylsulfonyl p-toluenesulfonyldiazomethane, 1-cyclo-hexylsulfonyl-1-(1,1-dimethylethylsulfonyl)diazomethane, bis(1,1-dimethylethylsulfonyl)-diazomethane, bis(1-methylethylsulfonyl)diazomethane, bis(cyclohexylsulfonyl)-diazomethane, 1-p-toluenesulfonyl-1-cyclohexylcarbonyl-diazomethane, 2-methyl-2-(p-toluenesulfonyl)propiophenone, 2-methane-sulfonyl-2-methyl-(4-methylthiopropiophenone, 2,4-methyl-2-(p-toluene-sulfonyl)pent-3-one, 1-diazo-1-methylsulfonyl-4-phenyl-2-butanone, 2-(cyclohexylcarbonyl-2-(p-toluene-sulfonyl)propane, 1-cyclohexylsulfonyl-1-cyclohexylcarbonyldiazomethane, 1-diazo-1-cyclohexylsulfonyl-3,3-dimethyl-2-butanone, 1-diazo-1-(1,1-dimethyl-ethylsulfonyl)-3,3-dimethyl-2-butanone, 1-acetyl-1-(1-methylethylsulfonyl)-diazomethane, 1-diazo-1-(p-toluenesulfonyl)-3,3-dimethyl-2-butanone, 1-diazo-1-benzenesulfonyl-3,3-dimethyl-2-butanone, 1-diazo-1-(p-toluenesulfonyl)-3-methyl-2-butanone, cyclohexyl 2-diazo-2-(p-toluenesulfonyl)acetate, tert-butyl 2-diazo-2-benzenesulfonylacetate, isopropyl-2-diazo-2-methanesulfonylacetate, cyclohexyl 2-diazo-2-benzenesulfonylacetate, tert-butyl-2-diazo-2-(p-toluenesulfonyl)acetate, 2-nitrobenzyl p-toluenesulfonate, 2,6-dinitrobenzyl p-toluenesulfonate, and 2,4-dinitrobenzyl p-trifluoro-methylbenzene-sulfonate.

The photosensitive composition contains alkali solubilizing groups protected by an acid sensitive group on a photoresist polymer or on a dissolution inhibitor. When the photoacid is generated, it catalyzes a deprotection reaction to unmask alkali solubilizing groups. These formerly protected alkali solubilizing groups now become alkali solubilizing groups. The starting polymer must be alkali soluble or, if it contains the protected alkali solubilizing groups, alkali soluble after deprotection. Suitable alkali solubilizing moieties include phenols, carboxylic acids, imides, hydroxyimides, sulfonamides, fluorinated alcohols, and kV the like. Examples of acid sensitive moieties include but are not limited to OC(=O)OtBu, tBu, acetals, CH2C(=O)OtBu, and 1-substituted cycloaliphatics. Examples of protected alkali solubilizing moieties include t-butyl esters, alpha alkoxyesters, 1,1 disubstituted esters, and alkoxyalkoxystyrenes.

Examples of suitable photoresist polymers include, but are not limited to, the resins described in U.S. Pat. No. 6,120,977, U.S. Pat. No. 6,136,504, U.S. Pat. No. 6,013,416, U.S. Pat. No. 5,985,522, U.S. Pat. No. 5,693,453, U.S. Pat. No. 4,491,628, WO 00/25178, WO 00/67072, JP 3-042618, JA 2000-275845, JA2000-137327, JA 09-73173 and U.S. Pat. No. 5,843,624, which are incorporated herein by reference. Blends of one or more photoresist resins may be used. Standard synthetic methods are typically employed to make the various types of suitable polymers. Procedures or references to suitable standard procedures (e.g., free radical polymerization) can be found in the cited patent applications.

Suitable specific polymer examples include but are not limited those shown below.

P1

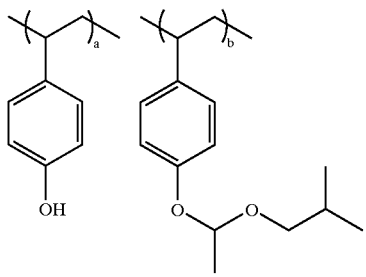

P2

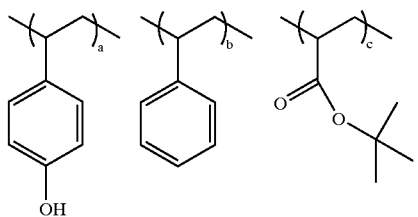

P3

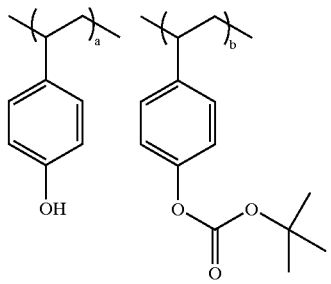

P4

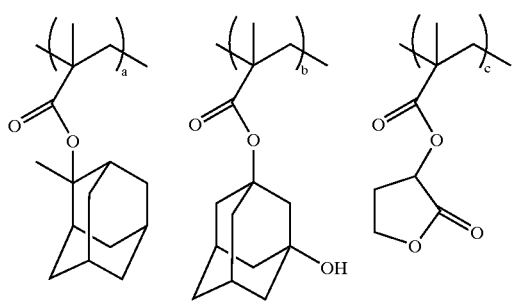

P5

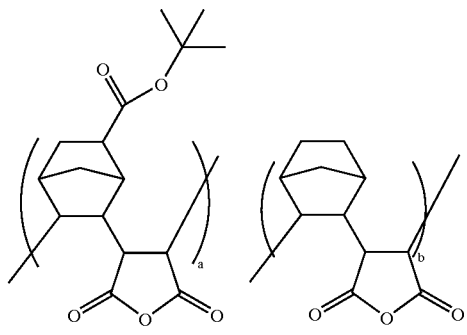

P6

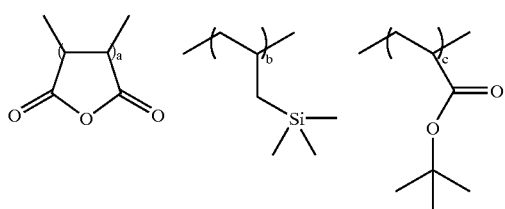

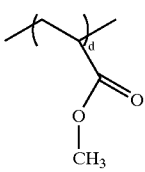

Suitable dissolution inhibitor compounds are compounds known in the art of about 3000 MW or less which contain alkali solublizing groups protected by an acid sensitive moiety. These dissolution inhibitors may by monomeric or oligomeric in nature. Preferred dissolution inhibitors will have carbonyl groups (e.g., those in carbonates or esters). Suitable dissolution inhibitors include, but are not limited, those shown below.

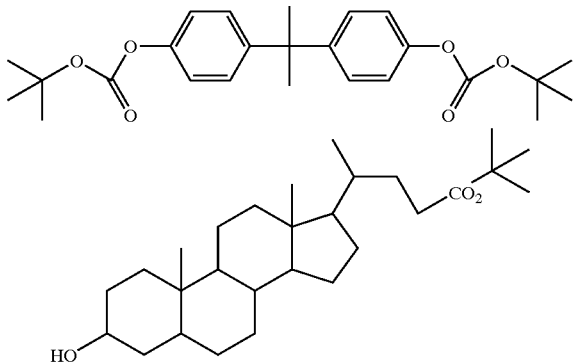

In an additional embodiment, base additives may be added to the photoresist composition. The purpose of the base additive is to scavenge protons present in the photoresist prior to being irradiated by the actinic radiation. The base prevents attack and cleavage of the acid labile groups by the undesirable acids, thereby increasing the performance and stability of the resist. The percentage of base in the composition should be significantly lower than the photoacid generator because it would not be desirable for the base to interfere with the cleavage of the acid labile groups after the photoresist composition is irradiated. The preferred range of the base compounds, when present, is about 3% to 50% by weight of the photoacid generator compound. Suitable examples of base additives are 2-methylimidazole, (2,6,di-isobutylphenyl)amine, triisopropylamine, tetramethyl ammonium hydroxide, tetrabutyl ammonium hydroxide, tris(methoxyethoxyethyl)amine (TMEA), tetrabutyl ammonium lactate (TBAL), 4-dimethylaminopryidine, 4,4'-diaminodiphenyl ether, 2,4,5-triphenylimidazole (TPI), 1,8-diazobicyclo[5.4.0]undec-7-ene (DBU), and 1,5-diazobicyclo[4.3.0]non-5-ene (DBN).

The photoresist composition may further comprise conventional additives, such as adhesion promoters, surfactants, dyes, and plasticizers.

Dyes may be added to the photoresist to increase the absorption of the composition to the actinic radiation wavelength. The dye must not poison the composition and must be capable of withstanding the process conditions including any thermal treatments. Examples of suitable dyes are fluorenone derivatives, anthracene derivatives or pyrene derivatives. Other specific dyes that are suitable for photoresist compositions are described in U.S. Pat. No. 5,593,812, which is incorporated herein by reference.

To make the photosensitive compositions of this invention, one or more of the suitable polymers and the PAGs of this invention are dissolved in a coating solvent along with any additives. The concentration of PAG in the solids portion of the resist (i.e., nonsolvent portions) may range from about 0.5% to about 15%. The preferred concentration range is from about 1% to about 6%. The concentration of the polymer in the solids portion of the resist may range from about 99% to about 60%.

The choice of solvent for the photoresist composition and the concentration thereof depends principally on the type of functionalities incorporated in the acid labile polymer, the photoacid generator, and the coating method. The solvent should be inert, dissolve all the components in the photoresist, not undergo any chemical reaction with the components and be re-removable on drying after coating. Suitable solvents for the photoresist composition may include ketones, ethers and esters, such as methyl ethyl ketone, methyl isobutyl ketone, 2-heptanone, cyclopentanone, cyclohexanone, 2-methoxy-1-propylene acetate, 2-methoxyethanol, 2-ethoxyethanol, 2-ethoxyethyl acetate, 1-methoxy-2-propyl acetate, 1,2-dimethoxy ethane ethyl acetate, cellosolve acetate, propylene glycol monoethyl ether acetate, methyl lactate, ethyl lactate, methyl pyruvate, ethyl pyruvate, methyl 3-methoxypropionate, ethyl 3-methoxypropionate, N-methyl-2-pyrrolidone, 1,4-dioxane, ethylene glycol monoisopropyl ether, diethylene glycol monoethyl ether, diethylene glycol monomethyl ether, diethylene glycol dimethyl ether, and the like.

The photoresist composition is applied uniformly to a substrate by known coating methods. For example, the coatings may be applied by spin-coating, dipping, knife coating, lamination, brushing, spraying, and reverse-roll coating. The coating thickness range generally covers values of about 0.1 to more than about 10 $\mu$m. After the coating operation, the solvent is generally removed by drying. The drying step is typically a heating step called 'soft bake' where the resist and substrate are heated to a temperature of about 50° C. to about 150° C. for about a few seconds to a few minutes; preferably for about 5 seconds to about 30 minutes depending on the thickness, the heating element and end use of the resist.

The photoresist compositions are suitable for a number of different uses in the electronics industry. For example, it can be used as electroplating resist, plasma etch resist, solder resist, resist for the production of printing plates, resist for chemical milling or resist in the production of integrated circuits. The possible coatings and processing conditions of the coated substrates differ accordingly.

For the production of relief structures, the substrate coated with the photoresist composition is exposed imagewise. The term 'imagewise' exposure includes both exposure through a photomask containing a predetermined pattern, exposure by means of a computer controlled laser beam which is moved over the surface of the coated substrate, exposure by means of computer-controlled electron beams, and exposure by means of X-rays or UV rays through a corresponding mask.

Radiation sources, which can be used, are all sources that emit radiation to which the photoacid generator is sensitive. Examples include high pressure mercury lamp, KrF excimer lasers, ArF excimer lasers, electron beams and x-rays sources.

The process described above for the production of relief structures preferably includes, as a further process measure, beating of the coating between exposure and treatment with the developer. With the aid of this heat treatment, known as "post-exposure bake", virtually complete reaction of the acid labile groups in the polymer resin with the acid generated by the exposure is achieved. The duration and temperature of this post-exposure bake can vary within broad limits and depend essentially on the functionalities of the polymer resin, the type of acid generator and on the concentration of these two components. The exposed resist is typically subjected to temperatures of about 50° C. to 150° C. for a few seconds to a few minutes. The preferred post exposure bake is from about 80° C. to about 130° C. for about 5 seconds to about 300 seconds.

After imagewise exposure and any heat treatment of the material, the exposed areas of the photoresist are removed by dissolution in a developer. The choice of the particular developer depends on the type of photoresist; in particular on the nature of the polymer resin or the photolysis products generated. The developer can include aqueous solutions of bases to which organic solvents or mixtures thereof may have been added. Particularly preferred developers are aqueous alkaline solutions. These include, for example, aqueous solutions of alkali metal silicates, phosphates, hydroxides and carbonates, but in particular of tetra alkylammonium hydroxides, and more preferably tetramethylammonium hydroxide (TMAH). If desired, relatively small amounts of wetting agents and/or organic solvents can also be added to these solutions.

After the development step, the substrate carrying the resist coating is generally subjected to at least one further treatment step which changes substrate in areas not covered by the photoresist coating. Typically, this can be implantation of a dopant, deposition of another material on the substrate or an etching of the substrate. This is usually followed by the removal of the resist coating from the substrate using a suitable stripping method.

The following examples are illustrative of the invention.

Synthetic Procedures

PAG SYNTHESIS EXAMPLE 1

Synthesis of 4-(1-butoxyphenyl)diphenylsulfonium mesylate

In a 500 mL, round bottom flask equipped with a reflux condenser was combined n-butyl phenyl ether (40.4 g, 0.269 mol), diphenylsulfoxide (48 g, 0.237 mol) and Eaton's Reagent (7.7% $P_2O_5$ in methanesulfonic acid) (154 g). An exothermic reaction occurred. The reaction mixture was maintained at 50–55° C. with stirring for 5 hours. The reaction mixture was then added to deionized water (1200 mL). This mixture was stirred for 30 minutes. The mixture was extracted two times with toluene (2×300 mL). The pH of the lower aqueous layer was adjusted to 8–8.5 by addition of a 25% aqueous solution of tetramethylammonium hydroxide (573 g).

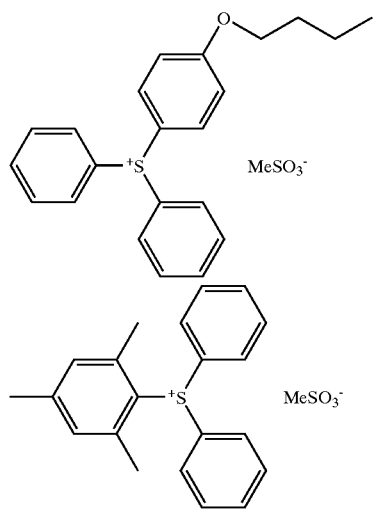

PAG SYNTHESIS EXAMPLE 2

Synthesis of 2,4,6-trimethylphenyldiphenylsulfonium mesylate

In a 1 L, round bottom flask equipped with a reflux condenser was combined 1,3,5-trimethylbenzene (40 g, 0.333 mol), diphenylsulfoxide (67.3 g, 0.333 mol) and Eaton's Reagent (160 g). An exothermic reaction occurred. The reaction mixture was maintained at 50–55° C. with stirring for 5 hours. The reaction mixture was then added to deionized water (800 mL). This mixture was stirred for 30 minutes. The mixture was extracted two times with toluene (2×250 mL). The pH of the lower aqueous layer was adjusted to 8–8.5 by addition of a 25% aqueous solution of tetramethylammonium hydroxide (889.6 g).

PAG SYNTHESIS EXAMPLE 3

Synthesis of 4-(1-butoxyphenyldiphenylsulfonium perfluoro(2-ethoxyethane)sulfonate (PAG 1)

To a solution of 21 grams water and 6.5 grams (0.02 moles) perfluoro(2-ethoxyethane)sulfonic acid was added 2.5 grams of 33% aqueous solution of sodium hydroxide. 261 grams of a 4% aqueous solution of 4-(1-butoxyphenyldiphenylsulfonium mesylate (from PAG Synthesis Example 1) was then added. Immediately a white suspension formed. 150 mL of chloroform was then added to this suspension. The resulting mixture was stirred for 16 hours. The lower chloroform solution layer was removed. The chloroform layer was washed six times with 75 mL portions of deionized water. The chloroform layer was then dried over magnesium sulfate. The magnesium sulfate was removed by filtration. Chloroform was removed from the filtrate on a rotary evaporator affording 13 grams of a viscous, yellow oil.

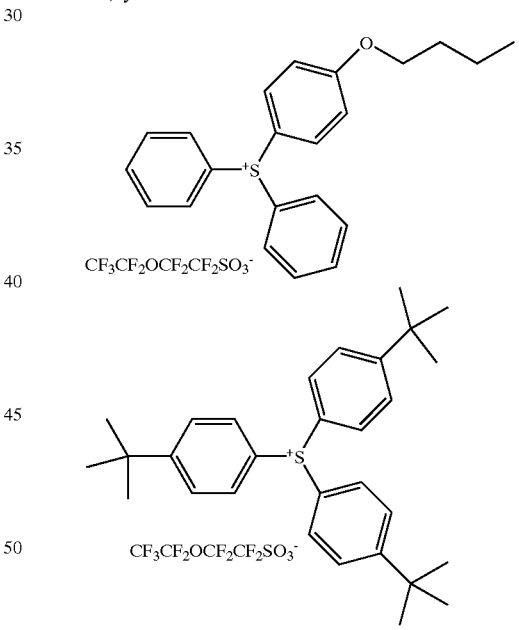

PAG SYNTHESIS EXAMPLE 4

Synthesis of tris(4-t-butylphenyl)sulfonium perfluoro(2-ethoxyethane)sulfonate

To a solution containing 2.04 g, 6.03 mmol PFEE-sodium salt in 54 grams water (prepared as in PAG Synthesis Example 3) was added 2.08 grams (4.02 mmol) of tris-(tert-butylphenyl)sulfonium tetrafluoroborate (Toyo Gosei) in 60 g of ethyl acetate. The resulting mixture was stirred for 24 hours. The bottom water layer was removed. The ethyl acetate layer (top) was washed four times with 30 ml portions of deionized water. The ethyl acetate layer was then dried over magnesium sulfate. The magnesium sulfate was removed by filtration. Ethyl acetate was removed from the filtrate on a rotary evaporator affording 2.5 grams of a white solid. The $^{19}F$ NMR spectrum contained the following resonance bands: δ −83.1(t, 2F), −87.7(s, 3F), −89.3(t, 2F), −118.9(s, 2F). The $^1H$ NMR contained: δ 1.4(s, 27H), 7.8(AB quartet, 12H).

PAG SYNTHESIS EXAMPLE 5

$CF_3OCF_2CF_2OCF_2CF_2SO_3Na$

Synthesis of perfluoro-4,7-dioxaheptyl-1-sodium sulfonate

A mixture of 1-bromo-perfluoro-2,5,8-trioxanonane ($CF_3OCF_2CF_2OCF_2CF_2OCF_2Br$) (2.8 g. 6.3 mmol) and sodium sulfite (0.83 g, 6.5 mmol) was dissolved in 20 ml of a 50:50 mixture of acetonitrile/water in a 50 ml round bottom flask equipped with a reflux condenser and a gas inlet. The mixture was heated to 70° C. Once reflux began and pressure equilibrium was reached, a rubber septum was placed on the gas inlet. The disappearance of starting material was monitored by GC using a FID detector. After 65 hrs no starting material was observed. The reaction mixture was filtered to remove sodium bromide. The remaining reaction mixture was vacuum stripped. A white solid was recovered. The $^{19}F$ spectra contained the following resonance bands δ −55.5(t, 3F), −78.2(t, 2F), −88.8(t, 2F), −91.1(q, 2F), −124.4(s, 2F). The spectral data indicates formation of $CF_3OCF_2CF_2OCF_2CF_2SO_3^-$ via cleavage of the $CF_2$—$OCF_2Br$ bond rather than formation of the expected $CF_3OCF_2CF_2OCF_2CF_2OCF_2SO_3^-$ product by cleavage of the $CF_2OCF_2$—$Br$ bond.

PAG SYNTHESIS EXAMPLE 6

Synthesis of 4-(1-butoxyphenyl)diphenylsulfonium perfluoro-4,7-dioxaheptyl-1-sulfonate An aqueous solution (17.35 g) of perfluoro-4,7-dioxaheptyl-1-sodium sulfonate (2.35 g, 5.8 mmol) (the product of PAG Synthesis Example 5) and an aqueous solution (17.5 g) of 4-(1-butoxyphenyl)diphenylsulfonium mesylate) (the product of PAG Synthesis Example 1) (2.5 g, 5.8 mmol) were combined in a 250 ml round bottom flask. A milky precipitate formed instantly. 50 ml of chloroform was added to the suspension. The resulting mixture was stirred for 24 hrs. The top layer was removed. The chloroform layer was washed four times with 20 ml portions of DI water. The chloroform layer was then dried over magnesium sulfate. The magnesium sulfate was removed by filtration. Chloroform was removed from the filtrate on a rotary evaporator affording 2.2 grams of a viscous oil. The $^1H$ NMR spectra contained the following resonance bands δ 1.0 (t, 3H), 1.5(sextet, 2H), 1.8(pentet, 2H), 4.2(t, 2H), 7.4(d, 2H), 7.9(multiplet, 12H). The $^{19}F$ NMR contained resonance bands at: δ −55.6(t, 3F), −77.0(t, 2F), −88.5(t, 2F), −91.1(q, 2F), −123.4(s, 2F).

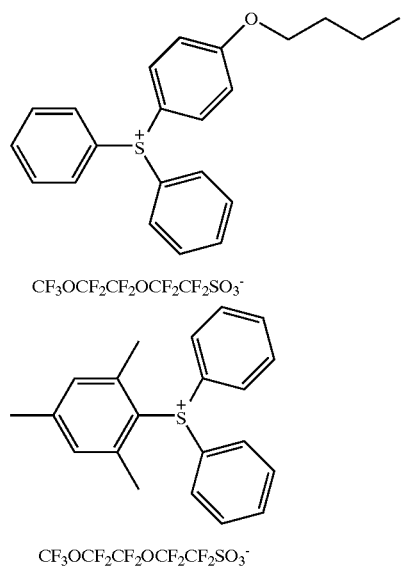

PAG SYNTHESIS EXAMPLE 7

Synthesis of 2,4,6-trimethylphenyldiphenylsulfonium perfluoro-4,7-dioxaheptyl-1-sulfonate An aqueous solution (2.5 ml) of perfluoro-4,7-dioxaheptyl-1-sodium sulfonate (the product of PAG Synthesis Example 5) (410 mg) and a aqueous solution (2.0 ml) of 2,4,6 trimethylphenyl sulfonium mesylate (320 mg) (the product of PAG Synthesis Example 2) were combined in a 15 ml round bottom flask. A milky precipitate formed instantly. The resulting mixture was stirred for 24 hrs. The solution became clear with a small amount of oil. The mixture was stripped until a white crystalline material was observed. The material was transferred to a 50 ml round bottom flask. A 20 ml aliquot of chloroform and a 1.5 ml aliquot of water was added to the flask. The water was split off. An additional water wash was done. The organic layer was dried over magnesium sulfate then filtered. A glass like material (0.16 g) was recovered. The $^1H$ NMR spectra contained the following resonance bands δ 2.2(s, 6H), 2.3(s, 3H), 7.3(s, 2H), 7.8(multiplet, 10H). The $^{19}F$ NMR contained resonance bands at: δ −55.6(t, 3F), −77.0(t, 2F), −88.5(t, 2F), −91.1(q, 2F).

PAG SYNTHESIS EXAMPLE 8

Synthesis of perfluoro-4-oxobutyl-1-sodium sulfonate

$CF_3OCF_2CF_2SO_3Na$

A mixture of 1-bromo-perfluoro-2,5,-dioxahexane ($CF_3OCF_2CF_2OCF_2Br$) (9.0 g, 27.2 mmol) and sodium sulfite (3.86 g, 30.6 mmol) was dissolved in 100 ml of a 50:50 mixture of acetonitrile/water in a 250 ml round bottom flask equipped with a reflux condenser and a gas inlet. The mixture was heated to 70° C. Once reflux began and pressure equilibrium was reached, a rubber septum was placed on the gas inlet. The disappearance of starting material was monitored by GC using a FID detector. After 137 hrs no starting material was observed. The reaction mixture was filtered to remove sodium bromide. The remaining reaction mixture was vacuum stripped. A white solid (6.9 g) was recovered. The $^{19}$F spectra contained the following resonance bands δ −55.7(t, 3F), −80.2(q, 2F), −124.5(s, 2F). The spectral data indicates formation of CF$_3$OCF$_2$CF$_2$SO$_3$— via cleavage of the CF$_2$—OCF$_2$Br bond rather than formation of the expected CF$_3$OCF$_2$CF$_2$OCF$_2$SO$_3$— by cleavage of the CF$_2$OCF$_2$—Br bond.

PAG SYNTHESIS EXAMPLE 9

Synthesis of 4-(1-butoxyphenyl)diphenylsulfonium perfluoro-4-oxobutyl-1-sulfonate An aqueous solution (16.70 g) of perfluoro-4-oxabutyl-1-sodium sulfonate (the product of PAG Synthesis Example 8) (1.7 g, 5.8 mmol) and an aqueous solution (17.5 g) of 4-(1-butoxyphenyl)diphenylsulfonium mesylate (the product of Synthesis Example 1) (2.5 g, 5.8 mmol) were combined in a 250 ml round bottom flask. A milky precipitate formed instantly. 50 ml of chloroform was added to the suspension. The resulting mixture was stirred for 24 hrs. The top layer was removed. The chloroform layer was washed four times with 20 ml portions of DI water. The chloroform layer was then dried over magnesium sulfate. The magnesium sulfate was removed by filtration. Chloroform was removed from the filtrate on a rotary evaporator affording 2.2 grains of a viscous oil. The $^1$H NMR spectra contained the following resonance bands δ 1.0(t, 3H), 1.5(sextet, 2H), 1.8(pentet, 2H), 4.2(t, 2H), 7.4(d, 2H), 7.9(multiplet, 12H). The $^{19}$F NMR contained resonance bands at: δ −55.1 (t, 3F), −79.4(q, 2F), −123.4(s, 2F).

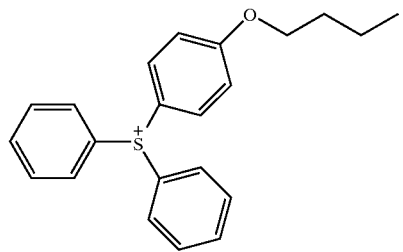

CF$_3$OCF$_2$CF$_2$SO$_3$⁻

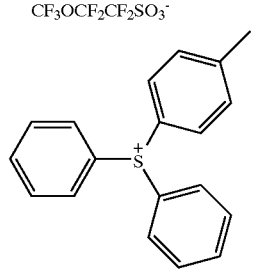

CF$_3$CF$_2$OCF$_2$CF$_2$SO$_3$⁻

PAG SYNTHESIS EXAMPLE 10

Synthesis of methylphenyl diphenyl sulfonium perfluoro(2-ethoxyethane)sulfonate

To solution containing 2.28 g, 6.75 mmol PFEE-sodium salt in 43 grams water (prepared as in PAG Synthesis Example 3) was added 2.73 grams (6.75 mmol) of methylphenyl diphenylsulfonium iodide (Toyo Gosei) in 10 ml of ethyl acetate. The resulting mixture was stirred for 18 hours. The bottom water layer was removed. The ethyl acetate layer (top) was washed four times with 30 ml portions of deionized water. The ethyl acetate layer was then dried over magnesium sulfate. The magnesium sulfate was removed by filtration. Ethyl acetate was removed from the filtrate on a rotary evaporator affording 2.9 grams of a viscous oil. The $^{19}$F NMR spectrum contained the following resonance bands: δ−83.2(t, 2F), −87.9(s, 3F), −89.4(t, 2F), −119.1(s, 2F). The $^1$H NMR contained resonance bands at: δ 2.5(s, 3H), 7.7(d, 2H), 7.9(multiplet, 12H).

COMPARATIVE PAG SYNTHESIS EXAMPLE 1

Synthesis of 2,4,6-trimethylphenyldiphenylsulfonium perfluorooctanesulfonate, (PAG 22)

To a solution of 260 grams water and 14.22 grams (0.023 moles) tetraethylammonium perfluorooctanesulfonate (Aldrich) was added 200 grams of 2,4,6-trimethylphenyldiphenylsulfonium mesylate prepared in PAG Synthesis Example 2. Immediately a white suspension formed. 250 mL of chloroform was then added to this suspension. The resulting mixture was stirred for 16 hours. The lower chloroform solution layer was removed. The chloroform layer was washed six times with 100 mL portions of deionized water. The chloroform layer was then dried over magnesium sulfate. The magnesium sulfate was removed by Filtration. Chloroform was removed from the filtrate on a rotary evaporator affording 17 grams of PAG 22.

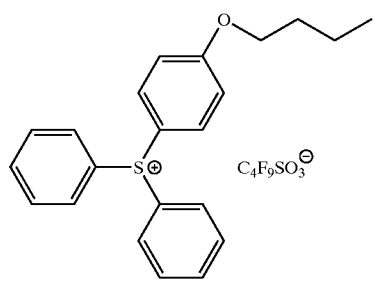

PAG 21

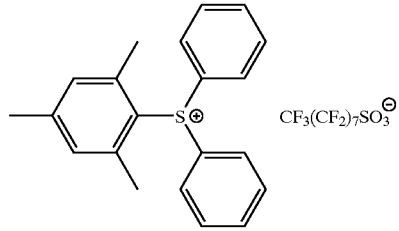

PAG 22

COMPARATIVE PAG SYNTHESIS EXAMPLE 2

Synthesis of 4-(1-butoxyphenyl)diphenylsulfonium perfluorobutanesulfonate (PAG 21)

To a solution of 200 grams water and 13.5 grams (0.0399 moles) potassium perfluorobutane-1-sulfonate was added 522 grams of a 4% aqueous solution of 4-(1-butoxyphenyl) diphenylsulfonium mesylate (prepared in PAG Synthesis Example 1). Immediately a white suspension was formed. 200 mL of chloroform was then added to this suspension. The resulting mixture was stirred for 16 hours. The lower chloroform solution layer was removed. The chloroform layer was washed six times with 200 mL portions of deionized water. The chloroform layer was then dried over magnesium sulfate. The magnesium sulfate was removed by filtration. Chloroform was removed from the filtrate on a rotary evaporator affording 19.3 grams of a white solid.

POLYMER SYNTHESIS EXAMPLE 1

Synthesis of poly(1-methylcyclohexylacrylate-co-norbornene-co-maleic anhydride)

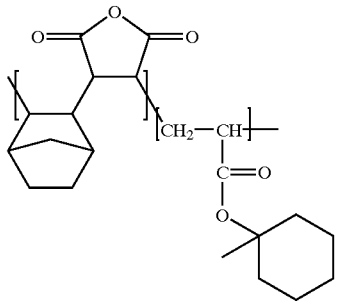

Norbornene (13.3 g, 0.141 moles), 1-methylcyclohexyl acrylate (20.37 g, 0.121 moles), maleic anhydride (13.8 g, 0.141 moles) and THF (35 mL) were charged in 3-neck flask equipped with overhead mechanical stirrer, and refluxed condenser. The polymerization mixture was kept under nitrogen all the time. The mixture was heated up to 95° C. for 2 hrs, cooled to 67° C. (oil bath temperature) and lauroyl peroxide (1.6 g) was added. Polymerization was run for 48 hrs at 67° C. Then the mixture was diluted with 100 mL THF and precipitated into 1 L of methyl-t-butyl ether/hexane mixture (50/50). The polymer was filtered, dissolved in 150 mL of THF and precipitated again into 1 L of methyl-t-butyl ether/hexane mixture (50/50). The polymer was filtered, dissolved in 150 mL of THF and precipitated a third time into 1 L of methyl-t-butyl ether/hexane mixture (50/50). The product was dried overnight at 55° C. in vacuum oven. Yield: 33.5 g (67%). Methyl cyclohexyl content=33% (mol) by TGA. MW=25495. Polydispersity=3.30.

POLYMER SYNTHESIS EXAMPLE 2

Preparation of 4-[1-(2-cyclohexylethoxy)-ethoxy]styrene-co-4-[1-(t-butoxy)-ethoxy]styrene-co-4-hydroxy styrene-co-4-t-butylstyrene copolymer A 250 mL round-bottom, three-necked flask was equipped with a temperature probe, a magnetic stir bar and closed vacuum adapter. 134.9 g of propylene glycol monomethyl ether acetate (PGMEA) was charged into the flask. 30.0 g of powdered poly(hydroxystyrene-co-t-butylstyrene) (93:7) (MW 12780; PD 1.9) was added to the stirring solvent. The mixture was stirred for 30 minutes to form a homogeneous solution. The mixture was heated to 60° C. and vacuum was applied to the solution to distill 48.92 g of the solvent. The solution was allowed to cool to room temperature under nitrogen atmosphere. 4.15 g of tertiary-butyl vinyl ether and 4.69 g 2-cyclohexylethanol were added to the homogeneous solution. 0.30 g of 1% para-toluene sulfonic acid (prepared by dissolving 1 g of acid in 99 g of PGMEA) was added. After a brief, mild exotherm, the solution was allowed to stir at 23° C. for 4 hours. 3.77 g of 1% triethylamine solution in PGMEA was added to the reaction mixture to quench the acid. The reaction mixture was stirred for an additional 30 minutes. The polymer solution was transferred to a 500 mL separatory funnel and treated with 115 g of acetone, 46 g of hexanes and 46 g of de-ionized water. The mixture was shaken for about 30 seconds to a minute and allowed to separate into two layers. The lower, aqueous layer was discarded. The top organic layer was subjected to two more washings. In the second washing, 23 g of acetone, 7 g of PGMEA and 23 g of deionized water were used and in the third washing, 17 g of acetone, 7 g of PGMEA and 23 g of deionized water were used. The top organic layer was transferred to a 500 mL round-bottom, three-necked flask equipped with a temperature probe, magnetic stir bar and a vacuum distillation assembly. The flask was placed on a heating mantle. Acetone and hexane were removed by atmospheric distillation. Water and some PGMEA were removed by azeotropic vacuum distillation at 66° C. until the solids content of the distillation flask was about 30.17%. Analytical data is found in the table. The structure of the polymer is given below (a=0.76; b=0.07; c=0.04; d=0.13).

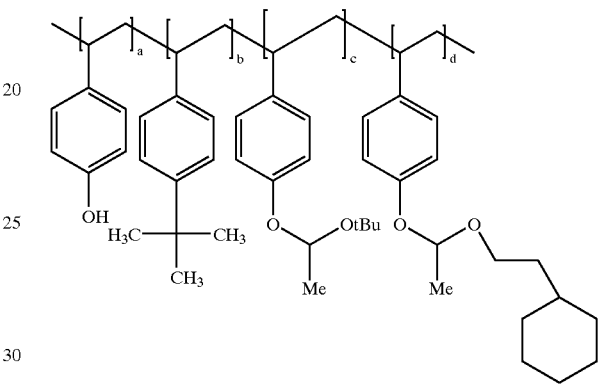

FORMULATION EXAMPLE 1

For 100 g of resist solution (total 9 weight % solids), 8.57 g of polymer P6 prepared according to procedures described in U.S. Pat. No. 6,165,682, 0.42 g of 4-(1-butoxyphenyl) diphenylsulfonium perfluoro(2-ethoxyethane)sulfonate (PAG 1) and 0.012 g of compound DBU (1,8-diazabicycloundec-7-ene, compound B1), were combined and dissolved in 91 g of propylene glycol methyl ether acetate (PGMEA). The mixture was rolled until the components dissolved. The solution was filtered through a 0.1μ Teflon filter.

COMPARATIVE FORMULATION EXAMPLE 1

For 100 g of resist solution (total 9 weight % solids), 8.57 g of polymer P6 prepared according to procedures described in U.S. Pat. No. 6,165,682, 0.41 g of photoacid generator PAG 21, and 0.011 g of compound DBU, were combined and dissolved in 91 g of propylene glycol methyl ether acetate (PGMEA). The mixture was rolled until the components dissolved. The solution was filtered through a 0.1μ Teflon filter.

COMPARATIVE FORMULATION EXAMPLE 2

For 100 g of resist solution (total 9 weight % solids), 8.47 g of polymer P6 prepared according to procedures described in U.S. Pat. No. 6,165,682, 0.52 g of photoacid generator PAG 22, and 0.014 g of compound DBU, were combined and dissolved in 91 g of propylene glycol methyl ether acetate (PGMEA). The mixture was rolled until the components dissolved. The solution was filtered through a 0.1μ Teflon filter.

LITHOGRAPHY EXAMPLE 1

Silicon wafers were spun coated with a thermally curable undercoat and post apply baked at 205° C. for 70 seconds, giving a 500 nm thick film. The undercoat was a phenolic copolymer crosslinked by hexamethoxymelamine under acid catalysis as described in U.S. application Ser. No. 09/268,430 filed Mar. 12, 1999, now U.S. Pat. No. 6,323,287, which is incorporated herein by reference.

Formulation Example 1 and Comparative Formulation Examples 1 and 2, were spin coated over the undercoat and post apply baked at 135° C. for 60 seconds giving a 235 nm thick film. The coated wafers were then exposed using a 0.6 NA ISI Microstepper outputting light from a 193 nm excimer laser. The wafers were post exposure baked at 125° C. for 60 seconds and developed for 60 seconds in 0.262 N tetramethylammonium hydroxide that contained a surfactant. The wafers were rinsed with de-ionized water and spun dry. The images were analyzed by scanning electron microscope.

RESULTS

| | $E_0$ | E1:1 (0.13μ dense line pattern) | Resolution | Depth of Focus (for 0.13μ dense line pattern) |
|---|---|---|---|---|
| Formulation Example 1 | 6.4 mJ/cm$^2$ | 20.5 mJ/cm$^2$ | 0.12μ | 0.5 μm |
| Comparative Formulation Example 1 | 5.6 mJ/cm$^2$ | 17 mJ/cm$^2$ | 0.12μ | 0.4 μm |
| Comparative Formulation Example 2 | 9.2 mJ/cm$^2$ | 30 mJ/cm$^2$ | 0.115μ | 0.5 μm |

Formulation Example 1 of this invention yielded a faster photospeed and better DOF than Comparative Formulation Example 1. Formulation Example 1 of this invention had comparable results to the environmentally unfriendly Comparative Formulation Example 2. Formulation Example 1 of this invention also had improved (less sloped) wall angles than Comparative Formulation Examples 1 and 2.

FORMULATION EXAMPLE 2

A formulation consisting of the polymer from Synthesis Example 2 (1.163 g), MWP-240 [4(1-ethoxyethoxy)styrene-co-4-hydroxystyrene 37:63, a product of Wako Chemical] (0.952 g), bis(t-butylsulfonyl)diazomethane (Wako Chemical) (0.124 g), 4-(1-butoxyphenyl)diphenylsulfonium perfluoro(2-ethoxyethane)sulfonate (0.079 g) (PAG 1 from PAG Synthesis Example 3), DBU (0.006 g), tris[2-(2-methoxyethoxy)ethyl]amine (0.001 g), antipyrene (0.003 g), PGMEA (16.5 g) and Silwet L-7210 (0.002 g) was mixed in an amber-bottle and stirred until a homogeneous solution was obtained. The solution was filtered through a 0.2 μm filter into a clean amber-bottle.

FORMULATION EXAMPLE 3

A formulation consisting of the polymer from Synthesis Example 2 (1.180 g), MWP-240 [4-(1-ethoxyethoxy)styrene-co-4-hydroxystyrene 37:63, [a product of Wako Chemical] (0.9653 g), bis(t-butylsulfonyl)diazomethane (0.132 g), tris(4-t-butylphenyl)sulfonium perfluoro(2-ethoxyethane)sulfonate (from PAG Synthesis Example 4) (0.110 g), DBU (0.007 g), tris[2-(2-methoxyethoxy)ethyl]amine (0.001 g), antipyrene (0.003 g), PGMEA (17.6 g) and Silwet L-7210 (0.002 g) was mixed in an amber-bottle and stirred until a homogeneous solution was obtained. The solution was filtered through a 0.2 μm filter into a clean amber-bottle.

LITHOGRAPHY EXAMPLE 2

Brewer Science's DUV42P BARC was used as an undercoat on silicon wafers. A 620 Å BARC coating was prepared by spin coating on top of a bare Si wafer and baking for 60 seconds at 200° C. 3250 Å Photoresist films of both Formulation Examples 2 and 3 were prepared by spin coating on top of the BARC and pre-exposure baking at 130° C. for 90 seconds. The photoresist was exposed on a Canon EX6 (NA=0.65) KrF 248 nm exposure system with annular illumination (sigma: 0.8/0.5) using a binary mask with line space patterns. The film was then post-exposure baked at 110° C. for 90 seconds and developed in a puddle of 0.26-N tetramethyl ammonium hydroxide for about 60 seconds, rinsed with de-ionized water and spun-dried. Formulation Example 2 resolved 0.130 μm line/space patterns (1:1 pitch) with about 0.80 micron DOF at an exposure of 60 mJ/cm$^2$. Formulation Example 3 resolved 0.130 μm line/space patterns (1:1 pitch) with about 0.80 micron DOF at an exposure of 66 mJ/cm$^2$.

FORMULATION EXAMPLE 4

A formulation consisting of the polymer from Polymer Synthesis Example 1 (2.019 g), 4(1-butoxyphenyl)diphenylsulfonium perfluoro(2-ethoxyethane) sulfonate (PAG 1 from PAG Synthesis Example 3) (0.075 g), TPI (2,4,5-triphenylimidazole) (0.004 g), PGMEA (12.9 g) and Silwet L-7210 (0.001 g) was mixed in an amber-bottle and stirred until a homogeneous solution was obtained. The solution was filtered through a 0.2 μm filter into a clean amber-bottle.

LITHOGRAPHY EXAMPLE 3

Brewer Science's DUV42 BARC was used as an undercoat on silicon wafers. A 550 Å BARC coating was prepared by spin coating on top of a bare Si wafer and baking for 60 seconds at 200° C. 4050 Å photoresist films of Formulation Example 4 were prepared by spin coating on top of the BARC and pre-exposure baking at 140° C. for 90 seconds. The photoresist was exposed on a Canon EX6 (NA=0.65) KrF 248 nm exposure system with annular illumination (sigma: 0.8/0.5) using a binary mask with line space patterns. The film was then post-exposure baked at 140° C. for 90 seconds and developed in a puddle of 0.26-N tetramethyl ammonium hydroxide for about 60 seconds, rinsed with de-ionized water and spun-dried. Formulation Example 4 resolved 0.140 μm line/space patterns (1:1 pitch) with about 0.70 micron DOF at an exposure of 36 mJ/cm$^2$.

FORMULATION EXAMPLE 5

A formulation consisting of polymer P6 (prepared according to procedures described in U.S. Pat. No. 6,165,682) (1.47 g), tris(4-t-butylphenyl)sulfonium perfluoro(2-ethoxyethane)sulfonate (0.144 g), DBU (0.011 g), and PGMEA (16.38 g) was mixed in an amber-bottle and stirred until a homogeneous solution was obtained. The solution was filtered through a 0.2 μm filter into a clean amber-bottle.

COMPARATIVE FORMULATION EXAMPLE 3

A formulation consisting of polymer P6 (prepared according to procedures described in U.S. Pat. No. 6,165,682) (1442.3 g), tris(4-t-butylphenyl)sulfonium nonafluorobutanesulfonate (Toyo Gosei) (138.6 g), DBU (10.68 g), PGMEA (16179 g) was mixed in a 5 gallon HDPE pail and stirred until a homogeneous solution was obtained. The solution was filtered twice through a 0.1 μm polypropylene filter into a clean amber-bottle.

LITHOGRAPHY EXAMPLE 4

2350 Å Photoresist films of both Formulation Examples 5 and Comparative Formulation Example 3 were prepared by spin coating on top of 5000 Å of an undercoat (prepared as described in Example 5 of co-pending U.S. application number (PCT/US02/07135) filed on Mar. 7, 2002, based upon U.S. Provisional Patent Application No. 60/275,528) and pre-exposure baking at 125° C. for 1.5 minute. The photoresist was exposed on a Canon EX6 (NA=0.65) KrF 248 nm exposure system with annular illumination (sigma: 0.8/0.5) using a binary mask having alternating line/space patterns. The film was then post-exposure baked at 115° C. for 90 seconds and developed in a puddle of aqueous 0.26-N tetramethyl ammonium hydroxide for 58 seconds after a 7 second spray, rinsed with de-ionized water and spun-dried. Formulation Example 5 resolved 0.14 μm line/space patterns (1:1 pitch) with about 0.8 micron DOF at an exposure of 39.25 mJ/cm$^2$. Comparative Formulation Example 3 resolved 0.14 μm line/space patterns (1:1 pitch) with about 0.8 micron DOF at an exposure of 35 mJ/cm$^2$. Formulation Example 5 showed improved profile DOF over Comparative Formulation Example 3.

FORMULATION EXAMPLE 6

A formulation consisting of polymer P6 (prepared according to procedures described in U.S. Pat. No. 6,165,682) (8.01 g), methylphenyl-diphenyl sulfonium perfluoro(2-ethoxyethane)sulfonate (PAG prepared in PAG Synthesis Example 10) (0.644 g), DBU (0.050 g), and PGMEA (111.3 g) was mixed in an amber-bottle and stirred until a homogeneous solution was obtained. The solution was filtered through a 0.2 μm filter into a clean amber-bottle.

COMPARATIVE FORMULATION EXAMPLE 4

A formulation consisting of polymer P6 (prepared according to procedures described in U.S. Pat. No. 6,165,682) (7.81 g), methylphenyl-diphenyl sulfonium perfluorooctanesulfonate (0.841 g), DBU (0.050 g), PGMEA (111.3 g) was mixed in an amber-bottle and stirred until a homogeneous solution was obtained. The solution was filtered through a 0.2 μm filter into a clean amber-bottle.

LITHOGRAPHY EXAMPLE 5

1700 Å Photoresist films of both Formulation Example 6 and Comparative Formulation Example 4 were prepared by spin coating on top of 5000 Å of an undercoat (prepared as described in U.S. application Ser. No. 09/268,430 filed Mar. 12, 1999, now U.S. Pat. No. 6,323,287, which is incorporated herein by reference) and pre-exposure baking at 125° C. for 1 minute. The coated wafers were then exposed using an ISI Microstepper (0.6 NA, annular illumination [sigma: 0.8/0.6]) outputting light from an ArF 193 nm excimer laser. A binary contact hole mask was used. The patterned wafers were post exposure baked at 115° C. for 60 seconds and developed for 60 seconds in 0.262 N aqueous tetramethylammonium hydroxide. The wafers were rinsed with de-ionized water and spun dry. The images were analyzed by scanning electron microscope. Formulation Example 6 resolved 0.135 μm contact holes (1:1 pitch) at an exposure of 52.5 mJ/cm$^2$. Comparative Formulation Example 4 also resolved 0.135 μm contact holes (1:1 pitch) at an exposure of 54.5 mJ/cm$^2$.

FORMULATION EXAMPLE 7

A formulation consisting of the polymer from Synthesis Example 2 (1.163 g), MWP-240 [4-(1-ethoxyethoxy) styrene-co-4-hydroxystyrene 37:63, [a product of Wako Chemical] (0.952 g), bis(t-butylsulfonyl)diazomethane (Wako Chemical) (0.124 g), 4-(1-butoxyphenyl) diphenylsulfonium perfluoro-4,7-dioxaheptyl-1-sulfonate (0.079 g) (from PAG Synthesis Example 6), DBU (0.006 g), tris[2-(2-methoxyethoxy)ethyl]amine (0.001 g), antipyrene (0.003 g), PGMEA (16.5 g) and Silwet L-7210 (0.002 g) was mixed in an amber-bottle and stirred until a homogeneous solution was obtained. The solution was filtered through a 0.2 μm filter into a clean amber-bottle.

FORMULATION EXAMPLE 8

A formulation consisting of the polymer from Synthesis Example 2 (1.163 g), MWP-240 [4 1-ethoxyethoxy)styrene-co-4-hydroxystyrene 37:63, a product of Wako Chemical] (0.952 g), bis(t-butylsulfonyl)diazomethane (Wako Chemical) (0.124 g), 2,4,6-trimethylphenyldiphenylsulfonium perfluoro-4,7-dioxaheptyl-1-sulfonate (0.079 g) (from PAG Synthesis Example 7), DBU (0.006 g), tris[2-(2-methoxyethoxy)ethyl] amine (0.001 g), antipyrene (0.003 g), PGMEA (16.5 g) and Silwet L-7210 (0.002 g) was mixed in an amber-bottle and stirred until a homogeneous solution was obtained. The solution was filtered through a 0.2 μm filter into a clean amber-bottle.

FORMULATION EXAMPLE 9

A formulation consisting of the polymer from Synthesis Example 2 (1.163 g), MWP-240 [4-(1-ethoxyethoxy) styrene-co-4-hydroxystyrene 37:63, [a product of Wako Chemical] (0.952 g), bis(t-butylsulfonyl)diazomethane (Wako Chemical) (0.124 g), 4-(1-butoxyphenyl) diphenylsulfonium perfluoro-4-oxobutyl-1-sulfonate (0.079 g) (from PAG Synthesis Example 9), DBU (0.006 g), tris[2-(2-methoxyethoxy)ethyl]amine (0.001 g), antipyrene (0.003 g), PGMEA (16.5 g) and Silwet L-7210 (0.002 g) was mixed in an amber-bottle and stirred until a homogeneous solution was obtained. The solution was filtered through a 0.2 μm filter into a clean amber-bottle.

LITHOGRAPHY EXAMPLE 6

Brewer Science's DUV42 BARC was used as an undercoat on silicon wafers. A 6000 Å BARC coating was prepared by spin coating on top of a bare Si wafer and baking for 60 seconds at 200° C. 3500 Å photoresist films of Formulation Examples 7–9 were prepared by spin coating on top of the BARC and pre-exposure baking at 130° C. for 90 seconds. The photoresist was exposed on a Canon EX6 (NA=0.65) KrF 248 nm exposure system with annular illumination (sigma: 0.8/0.5) using a binary mask with line space patterns. The film was then post-exposure baked at 110° C. for 90 seconds and developed in a puddle of 0.26-N tetramethyl ammonium hydroxide for about 60 seconds, rinsed with de-ionized water and spun-dried. Formulation Example 7 resolved 0.150 μm line/space patterns (1:1 pitch) with about 1.0 micron DOF at an exposure of 48 mJ/cm$^2$. Formulation Example 8 resolved 0.160 μm line/space patterns (1:1 pitch) with about 0.40 micron DOF at an exposure of 65 mJ/cm$^2$. Formulation Example 9 resolved 0.150 μm line/space patterns (1:1 pitch) with about 0.90 micron DOF at an exposure of 36 mJ/cm$^2$.

FORMULATION EXAMPLE 10

For 15 g of resist solution (total 13 weight % solids), 1.89 g of polymer P5, which is prepared by procedures as described in Japanese Kokai JA-10-254139, which is incorporated by reference, 0.58 g of PAG 2, 0.004 g of TMEA, and 0.001 g of quencher tetrabutylammonium hydroxide are combined and dissolved in 13.05 g of propylene glycol methyl ether acetate (PGMEA). The mixture is rolled until the components dissolve, and the solution filtered through 0.1μ Teflon filter.

FORMULATION EXAMPLE 11

For 15 g of resist solution (total 2.2 weight % solids), 2.85 g of polymer P4 that is prepared by procedures as described in U.S. Pat. No. 5,635,332, and 0.15 g of PAG 2 are combined and dissolved in 12 g of cyclohexanone. The mixture is rolled until the components dissolve, and the solution filtered through 0.1 μd Teflon filter.

FORMULATION EXAMPLE 12

For 61 g of resist solution (total 18 weight % solids), 10 g of polymer P4 which is prepared by procedures as described in European patent application EP 1 041 442 A1, 0.5 g of PAG 2, 0.5 g of PAG 4, and 0.015 g of (2,6-di-isobutylphenyl)amine are combined and dissolved in mixture consisting of 47.5 g of propylene glycol methyl ether acetate and 2.5 g of γ-butyrolactone. The mixture is rolled until the components dissolve, and the solution filtered through 0.1μ Teflon filter.

LITHOGRAPHY EXAMPLE 7

The resist formulations of Example 10–12 are spin coated on primed silicon wafers and post apply baked at 120° C. for 60 seconds giving a 235 nm thick film. The coated wafers are then exposed using a 0.6 NA ISI Microstepper ArF laser outputting light at 193 nm. The wafers are post exposure baked at 125° C. for 60 seconds and developed for 60 seconds in 0.262 N tetramethylammonium hydroxide that contained a surfactant. The wafers are rinsed with de-ionized water and spun dry. The images are analyzed by scanning electron microscope. Formulation Examples 10–12 yield excellent images with good photospeed, resolution, and near vertical and smooth sidewalls.

FORMULATION EXAMPLE 13

For 30 g of resist solution (total 16 weight % solids), 4.604 g of polymer P2 which is prepared by procedures as described in U.S. Pat. No. 5,861,231, 0.186 g of PAG 3, and 0.014 g of TBAL are combined and dissolved in 25.197 g of ethyl lactate. The mixture is rolled until the components dissolve, and the solution filtered through 0.1μ Teflon filter.

FORMULATION EXAMPLE 14

For 36.05 g of resist solution (total 18 weight % solids), 4.5 g of polymer P1 which is prepared by procedures as described in EP 1024406A1, 1.5 g of polymer P3, 0.3 g of PAG 19, 0.05 g PAG 11, and 0.1 g of TMEA, are combined and dissolved in 28.7 g of propylene glycol methyl ether. The mixture is rolled until the components dissolve, and the solution filtered through 0.1μ Teflon filter.

LITHOGRAPHY EXAMPLE 8

2350 Å Photoresist films of both Formulation Examples 13 and 14 are prepared by spin coating on top of primed silicon wafers and pre-exposure baking at 125° C. for 1.5 minute. The photoresists are exposed on a Canon EX6 (NA=0.65) KrF 248 nm exposure system with annular illumination (sigma: 0.8/0.5) using a binary mask having alternating line/space patterns. The films are then post-exposure baked at 115° C. for 90 seconds and developed in a puddle of aqueous 0.26-N tetramethyl ammonium hydroxide for 58 seconds after a 7 second spray, rinsed with de-ionized water and spun-dried. Formulation Examples 13 and 14 yield excellent images with good photospeed, resolution, and near vertical and smooth sidewalls.

What is claimed is:

1. A photoacid compound having the following general structure:

wherein n is an integer between about 1 to 4; R is selected from the group consisting of: substituted or unsubstituted $C_1$–$C_{12}$ linear or branched alkyl or alkenyl, substituted or unsubstituted araalkyl, substituted or unsubstituted aryl, substituted or unsubstituted bicycloalkyl, substituted or unsubstituted tricycloalkyl, hydrogen, alkyl sulfonic acid, substituted or unsubstituted perfluoroalkyl, the general structure $F((CF_2)_pO)_m(CF_2)_q$— wherein p is between about 1 to 4, m is between about 0 to 3 and q is between about 1 to 4, and substituted or unsubstituted partially fluorinated alkyl, halofluoroalkyl, perfluoroalkylsulfonic, and glycidyl; and X is covalently bonded organic radicals selected from the group consisting of: sulfonic esters of polyhydroxyphenols and alpha sulfonyloxyketones.

2. A photoacid compound according to claim 1 wherein the compound is a sulfonic acid ester of polyhydroxyphenol having the general structure:

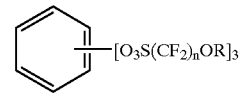

wherein n is an integer between about 1 to 4; and R is selected from the group consisting of: substituted or unsubstituted $C_1$–$C_{12}$ linear or branched alkyl or alkenyl, substituted or unsubstituted araalkyl, substituted or unsubstituted aryl, substituted or unsubstituted bicycloalkyl, substituted or unsubstituted tricycloalkyl, hydrogen, alkyl sulfonic acid, substituted or unsubstituted perfluoroalkyl, the general structure $F((CF_2)_pO)_m(CF_2)_q$— wherein p is between about 1 to 4, m is between about 0 to 3 and q is between about 1 to 4, and substituted or unsubstituted partially fluorinated alkyl, halofluoroalkyl, perfluoroalkylsulfonic, and glycidyl.

3. A photoacid compound according to claim 1 wherein the compound is an alpha sulfonyloxyketone having the general formula:

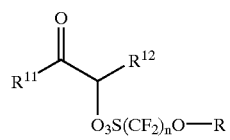

wherein n is an integer between about 1 to 4; and R is selected from the group consisting of: substituted or unsubstituted $C_1$–$C_{12}$ linear or branched alkyl or alkenyl, substituted or unsubstituted araalkyl, substituted or unsubstituted aryl, substituted or unsubstituted bicycloalkyl, substituted or unsubstituted tricycloalkyl, hydrogen, alkyl sulfonic acid, substituted or unsubstituted perfluoroalkyl, and the general structure $F((CF_2)_pO)_m(CF_2)_q$— wherein p is between about 1 to 4, m is between about 0 to 3 and q is between about 1 to 4, and substituted or unsubstituted partially fluorinated alkyl, halofluoroalkyl, perfluoroalkylsulfonic, and glycidyl; and $R^{11}$ and $R^{12}$ are substituted or unsubstituted alkyl or aryl.

4. A photoresist composition comprising:
a polymer; and
a photoacid compound having the following general structure:

R—O(CF$_2$)$_n$SO$_3$X wherein n is an integer between about 1 to 4; R is selected from the group consisting of: substituted or unsubstituted $C_1$–$C_{12}$ linear or branched alkyl or alkenyl, substituted or unsubstituted araalkyl, substituted or unsubstituted aryl, substituted or unsubstituted bicycloalkyl, substituted or unsubstituted tricycloalkyl, hydrogen, alkyl sulfonic acid, substituted or unsubstituted perfluoroalkyl, the general structure F((CF$_2$)$_p$O)$_m$(CF$_2$)$_q$— wherein p is between about 1 to 4, m is between about 0 to 3 and q is between about 1 to 4, and substituted or unsubstituted partially fluorinated alkyl, halofluoroalkyl, perfluoroalkylsulfonic, and glycidyl; and X is covalently bonded organic radicals selected from the group consisting of: sulfonic esters of polyhydroxyphenols and alpha sulfonyloxyketones.

5. A photoresist composition according to claim 4 wherein the photoactive compound is a compound of the following general structure:

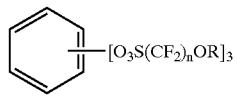

wherein n is an integer between about 1 to 4; and R is selected from the group consisting of: substituted or unsubstituted $C_1$–$C_{12}$ linear or branched alkyl or alkenyl, substituted or unsubstituted araalkyl, substituted or unsubstituted aryl, substituted or unsubstituted bicycloalkyl, substituted or unsubstituted tricycloalkyl, hydrogen, alkyl sulfonic acid, substituted or unsubstituted perfluoroalkyl, the general structure F((CF$_2$)$_p$O)$_m$(CF$_2$)$_q$— wherein p is between about 1 to 4, m is between about 0 to 3 and q is between about 1 to 4, and substituted or unsubstituted partially fluorinated alkyl, halofluoroalkyl, perfluoroalkylsulfonic, and glycidyl.

6. A photoresist composition according to claim 4 wherein the photoactive compound is an alpha sulfonyloxyketone having the general formula:

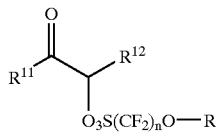

wherein n is an integer between about 1 to 4; and R is selected from the group consisting of: substituted or unsubstituted $C_1$–$C_{12}$ linear or branched alkyl or alkenyl, substituted or unsubstituted araalkyl, substituted or unsubstituted aryl, substituted or unsubstituted bicycloalkyl, substituted or unsubstituted tricycloalkyl, hydrogen, alkyl sulfonic acid, substituted or unsubstituted perfluoroalkyl, and the general structure F((CF$_2$)$_p$O)$_m$(CF$_2$)$_q$— wherein p is between about 1 to 4, m is between about 0 to 3 and q is between about 1 to 4, and substituted or unsubstituted partially fluorinated alkyl, halofluoroalkyl, perfluoroalkylsulfonic, and glycidyl; and $R^{11}$ and $R^{12}$ are substituted or unsubstituted alkyl or aryl.

7. A photoresist composition according to claim 4 wherein the polymer is a silicon-containing polymer having alkali solubilizing groups protected by an acid sensitive group.

8. A photoresist composition according to claim 7 wherein the polymer has the units

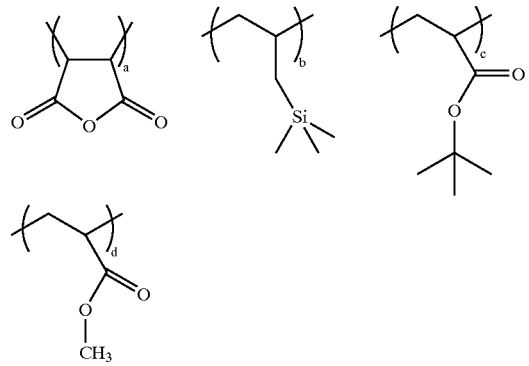

in the polymer.

9. A method for fabricating an integrated circuit which comprises:
depositing a photoresist composition of claim 4 on a substrate,
irridating said photoresist composition, thereby generating a fluorinated alkyl sulfonic acid with a short perfluoroalkyl chain attached to an ether linkage.

10. A method for fabricating an integrated circuit which comprises:
depositing a photoresist composition of claim 5 on a substrate,
irridating said photoresist composition, thereby generating a fluorinated alkyl sulfonic acid with a short perfluoroalkyl chain attached to an ether linkage.

11. A method for fabricating an integrated circuit which comprises:
depositing a photoresist composition of claim 6 on a substrate,
irridating said photoresist composition, thereby generating a fluorinated alkyl sulfonic acid with a short perfluoroalkyl chain attached to an ether linkage.

12. A method for fabricating an integrated circuit which comprises:
depositing a photoresist composition of claim 7 on a substrate,
irridating said photoresist composition, thereby generating a fluorinated alkyl sulfonic acid with a short perfluoroalkyl chain attached to an ether linkage.

13. A method for fabricating an integrated circuit which comprises:
depositing a photoresist composition of claim 8 on a substrate,
irridating said photoresist composition, thereby generating a fluorinated alkyl sulfonic acid with a short perfluoroalkyl chain attached to an ether linkage.

14. A photoresist composition comprising:
a polymer that is a silicon-containing polymer having alkali solubilizing groups protected by an acid sensitive group; and
a photoacid compound having the following general structure:

wherein n is an integer between about 1 to 4; R is selected from the group consisting of: substituted or unsubstituted $C_1$–$C_{12}$ linear or branched alkyl or alkenyl, substituted or unsubstituted araalkyl, substituted or unsubstituted aryl, substituted or unsubstituted bicycloalkyl, substituted or unsubstituted tricycloalkyl, hydrogen, alkyl sulfonic acid, substituted or unsubstituted perfluoroalkyl, the general structure $F((CF_2)_pO)_m(CF_2)_q$ — wherein p is between about 1 to 4, m is between about 0 to 3 and q is between about 1 to 4, and substituted or unsubstituted partially fluorinated alkyl, halofluoroalkyl, perfluoroalkylsulfonic, and glycidyl; and X is selected from the group consisting of: organic iodonium cations, organic sulfonium cations except trimethyl sulfonium cations, and covalently bonded organic radicals selected from the group consisting of: oxime sulfonates, N-hydroxyimide sulfonates, substituted or unsubstituted nitrobenzyl esters, sulfonic esters of polyhydroxyphenols and alpha sulfonyloxyketones.

15. A photoresist composition according to claim 14 wherein the silicon-containing polymer has the units

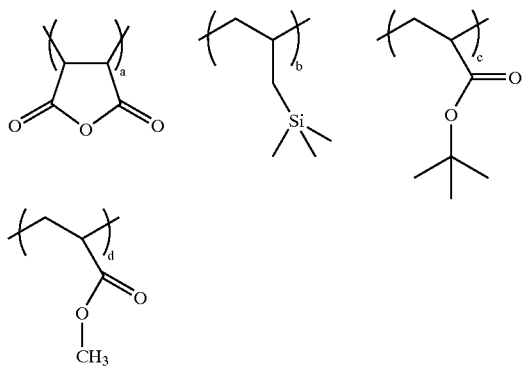

in the polymer.

16. A photoresist composition according to claim 14 wherein the photoacid compound is a compound wherein the sulfonium cation is selected from the group consisting of:

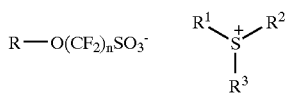

wherein $R^1$, $R^2$ and $R^3$ are not all simultaneously methyl, and

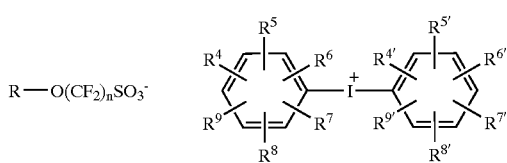

where $R^1$, $R^2$, and $R^3$ are individually selected from substituted or unsubstituted aryl and alkyl; $R^4$, $R^5$, $R^6$, $R^7$, $R^8$, $R^{4'}$, $R^{5'}$, $R^{6'}$, $R^{7'}$ and $R^{8'}$ are individually selected from the group consisting of: branched, linear, or cyclic alkyl, branched, linear, or cyclic alkoxy, halogen, hydrogen, $OCO_2G$, $OCH_2CO_2G$, and OG, where G is an acid sensitive group.

17. A photoresist composition according to claim 14 wherein the photoactive compound wherein said sulfonium cation is selected from the group consisting of:

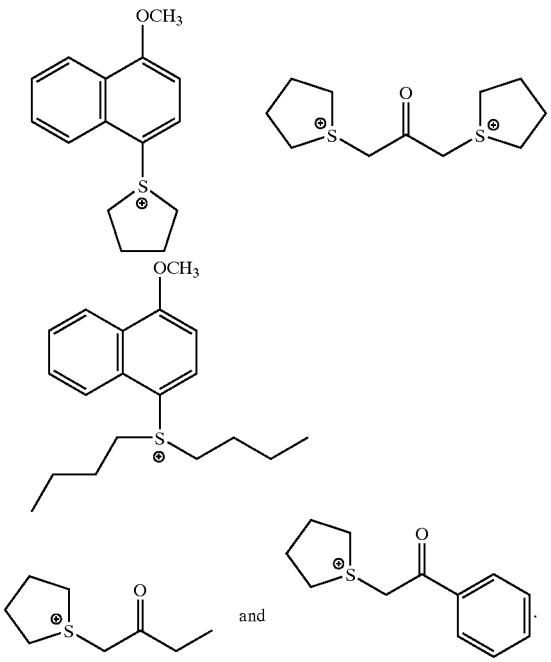

18. A photoresist composition according to claim 14 wherein in the photoactive compound the oxime sulfonate has the general structure:

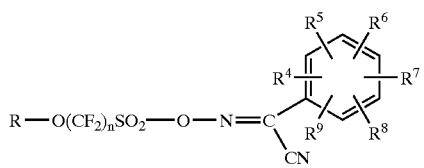

wherein n is an integer between about 1 to 4; R is selected from the group consisting of: substituted or unsubstituted $C_1$–$C_{12}$ linear or branched alkyl or alkenyl, substituted or unsubstituted araalkyl, substituted or unsubstituted aryl, substituted or unsubstituted bicycloalkyl, substituted or unsubstituted tricycloalkyl, hydrogen, alkyl sulfonic acid, substituted or unsubstituted perfluoroalkyl, the general structure $F((CF_2)_pO)_m(CF_2)_q$— wherein p is between about 1 to 4, m is between about 0 to 3 and q is between about 1 to 4, and substituted or unsubstituted partially fluorinated alkyl, halofluoroalkyl, perfluoroalkylsulfonic, and glycidyl, and $R^4$, $R^5$, $R^6$, $R^7$ and $R^8$ are individually selected from the group consisting of: branched, linear, or cyclic alkyl, branched, linear, or cyclic alkoxy, halogen, hydrogen, $OCO_2G$, $OCH_2CO_2G$, and OG, where G is an acid sensitive group.

19. A photoresist composition according to claim 14 wherein in the photoactive compound the N-hydroxyimide sulfonate has the general formula:

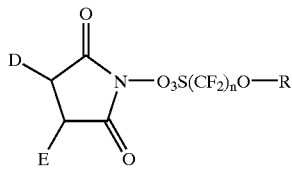

where D and E are independently H, substituted or unsubstituted aryl or together compose a substituted or unsubstituted bicyclic, or tricyclic alicyclic ring system; n is an integer between about 1 to 4; and R is selected from the group consisting of: substituted or unsubstituted $C_1$–$C_{12}$ linear or branched alkyl or alkenyl, substituted or unsubstituted araalkyl, substituted or unsubstituted aryl, substituted or unsubstituted bicycloalkyl, substituted or unsubstituted tricycloalkyl, hydrogen, alkyl sulfonic acid, substituted or unsubstituted perfluoroalkyl, the general structure $F((CF_2)_p O)_m(CF_2)_q$— wherein p is between about 1 to 4, m is between about 0 to 3 and q is between about 1 to 4, and substituted or unsubstituted partially fluorinated alkyl, halofluoroalkyl, perfluoroalkylsulfonic, and glycidyl.

20. A photoresist composition according to claim 14 wherein in the photoactive compound the nitrobenzyl ester has the formula:

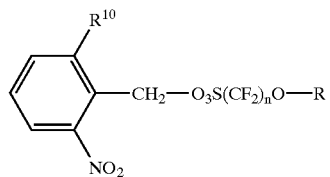

wherein $R^{10}$ is an electron withdrawing substituent; n is an integer between about 1 to 4; and R is selected from the group consisting of: substituted or unsubstituted $C_1$–$C_{12}$ linear or branched alkyl or alkenyl, substituted or unsubstituted araalkyl, substituted or unsubstituted aryl, substituted or unsubstituted bicycloalkyl, substituted or unsubstituted tricycloalkyl, hydrogen, alkyl sulfonic acid, substituted or unsubstituted perfluoroalkyl, the general structure $F((CF_2)_p O)_m(CF_2)_q$— wherein p is between about 1 to 4, m is between about 0 to 3 and q is between about 1 to 4, and substituted or unsubstituted partially fluorinated alkyl, halofluoroalkyl, perfluoroalkylsulfonic, and glycidyl.

21. A photoresist composition according to claim 14 wherein the photoactive compound is selected from the group consisting of:

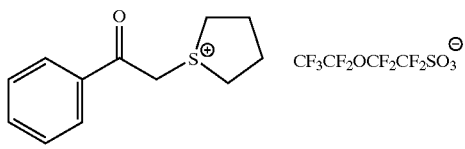

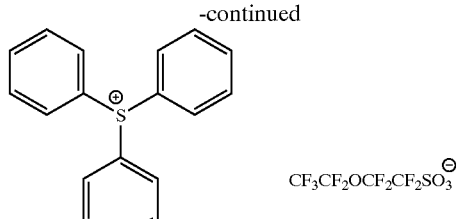

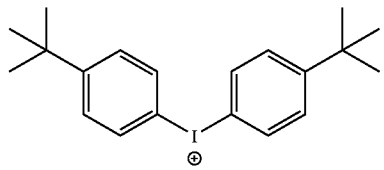

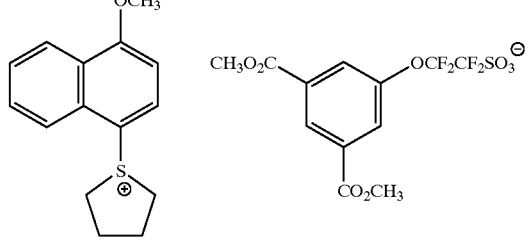

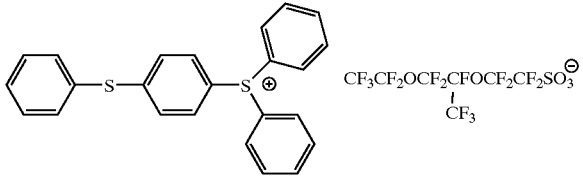

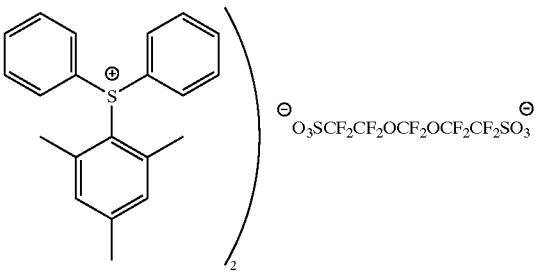

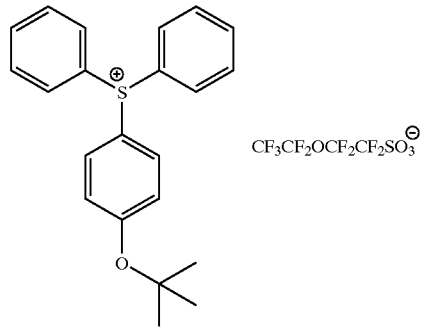

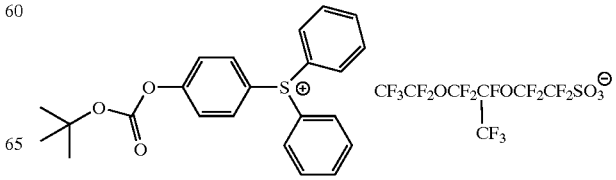

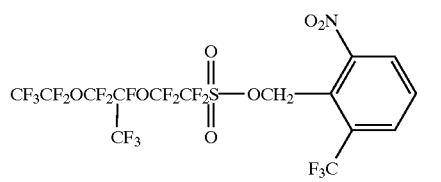
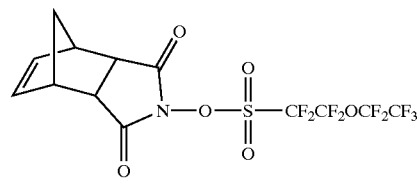
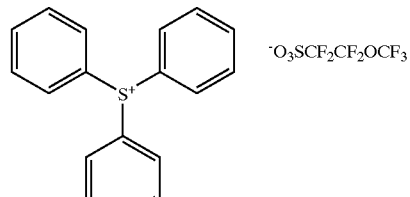
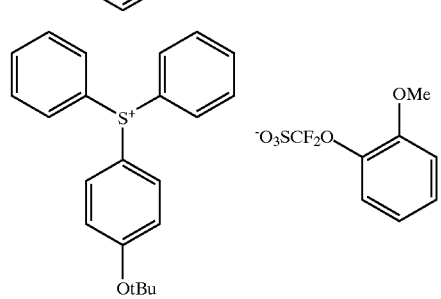
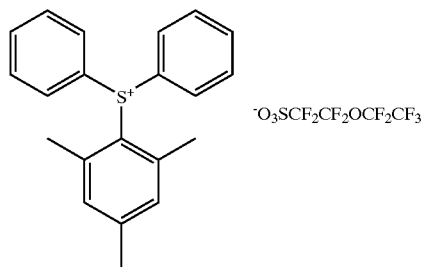
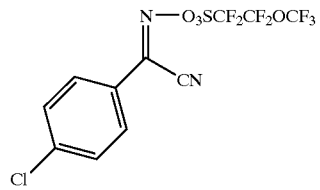
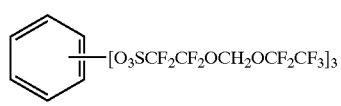
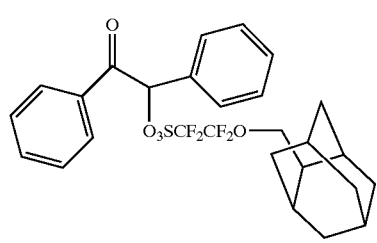
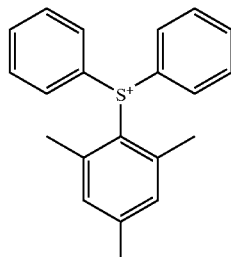
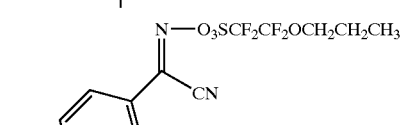
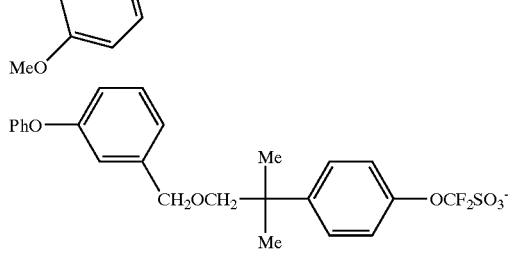
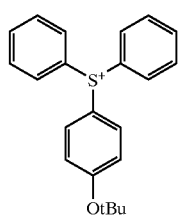
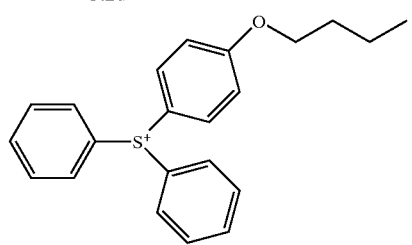
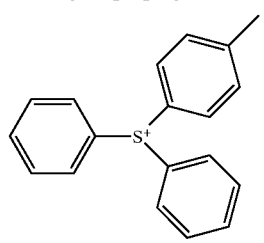
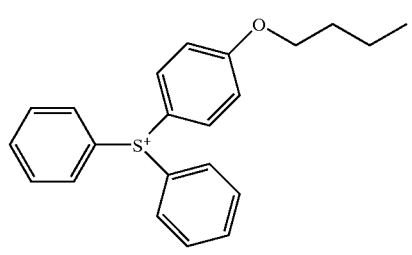

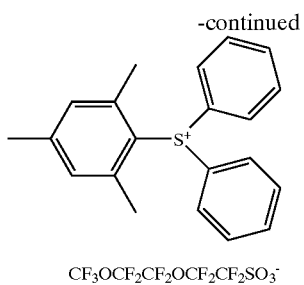

CF₃OCF₂CF₂OCF₂CF₂SO₃⁻

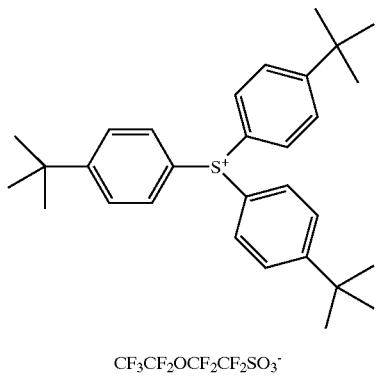

CF₃CF₂OCF₂CF₂SO₃⁻

22. A method for fabricating an integrated circuit which comprises:
depositing a photoresist composition of claim 14 on a substrate,
irridating said photoresist composition, thereby generating a fluorinated alkyl sulfonic acid with a short perfluoroalkyl chain attached to an ether linkage.

23. A method for fabricating an Integrated circuit which comprises:
depositing a photoresist composition of claim 15 on a substrate,
irridating said photoresist composition, thereby generating a fluorinated alkyl sulfonic acid with a short perfluoroalkyl chain attached to an ether linkage.

24. A method for fabricating an integrated circuit which comprises:
depositing a photoresist composition of claim 16 on a substrate,
irridating said photoresist composition, thereby generating a fluorinated alkyl sulfonic acid with a short perfluoroalkyl chain attached to an ether linkage.

25. A method for fabricating an integrated circuit which comprises:
depositing a photoresist composition of claim 17 on a substrate,
irridating said photoresist composition, thereby generating a fluorinated alkyl sulfonic acid with a short perfluoroalkyl chain attached to an ether linkage.

26. A method for fabricating an integrated circuit which comprises:
depositing a photoresist composition of claim 18 on a substrate,
irridating said photoresist composition, thereby generating a fluorinated alkyl sulfonic acid with a short perfluoroalkyl chain attached to an ether linkage.

27. A method for fabricating an integrated circuit which comprises:
depositing a photoresist composition of claim 19 on a substrate,
irridating said photoresist composition, thereby generating a fluorinated alkyl sulfonic acid with a short perfluoroalkyl chain attached to an ether linkage.

28. A method for fabricating an integrated circuit which comprises:
depositing a photoresist composition of claim 20 on a substrate, irridating said photoresist composition, thereby generating a fluorinated alkyl sulfonic acid with a short perfluoroalkyl chain attached to an ether linkage.

29. A method for fabricating an integrated circuit which comprises:
depositing a photoresist composition of claim 21 on a substrate,
irridating said photoresist composition, thereby generating a fluorinated alkyl sulfonic acid with a short perfluoroalkyl chain attached to an ether linkage.

* * * * *